(12) United States Patent
Lee et al.

(10) Patent No.: US 10,772,943 B2
(45) Date of Patent: Sep. 15, 2020

(54) LIQUID FORMULATION CONTAINING BOTULINUM TOXIN AND STABILIZING AGENT, AND PREPARATION METHOD THEREFOR

(71) Applicant: Hugel Inc., Gangwon-do (KR)

(72) Inventors: Chee Gun Lee, Gyeonggi-do (KR); Ji Hyun Oum, Gyeonggi-do (KR)

(73) Assignee: HUGEL INC., Chuncheon-si (KR)

( * ) Notice: Subject to any disclaimer, the term of this patent is extended or adjusted under 35 U.S.C. 154(b) by 0 days.

(21) Appl. No.: 16/327,390

(22) PCT Filed: Aug. 28, 2017

(86) PCT No.: PCT/KR2017/009383
§ 371 (c)(1),
(2) Date: Feb. 22, 2019

(87) PCT Pub. No.: WO2018/038585
PCT Pub. Date: Mar. 1, 2018

(65) Prior Publication Data
US 2019/0201506 A1 Jul. 4, 2019

(30) Foreign Application Priority Data

Aug. 26, 2016 (KR) .................. 10-2016-0109558
Aug. 31, 2016 (WO) ............. PCT/KR2016/009706
Aug. 25, 2017 (KR) .................. 10-2017-0108180
Aug. 25, 2017 (KR) .................. 10-2017-0108181

(51) Int. Cl.

| A61K 39/00 | (2006.01) |
|---|---|
| A61K 39/02 | (2006.01) |
| A61K 39/08 | (2006.01) |
| A61K 38/48 | (2006.01) |
| A61K 9/08 | (2006.01) |
| A61K 31/167 | (2006.01) |
| A61K 47/18 | (2017.01) |
| A61K 47/12 | (2006.01) |
| A61K 47/08 | (2006.01) |
| A61K 47/26 | (2006.01) |
| A61K 9/00 | (2006.01) |

(52) U.S. Cl.
CPC ........ *A61K 38/4893* (2013.01); *A61K 9/0019* (2013.01); *A61K 9/08* (2013.01); *A61K 31/167* (2013.01); *A61K 38/48* (2013.01); *A61K 47/08* (2013.01); *A61K 47/12* (2013.01); *A61K 47/18* (2013.01); *A61K 47/183* (2013.01); *A61K 47/26* (2013.01); *C12Y 304/24069* (2013.01)

(58) Field of Classification Search
CPC ...... A61K 38/164; A61K 39/00; A61K 39/02; A61K 39/08
USPC ......... 424/184.1, 234.1, 236.1, 239.1, 247.1, 424/278.1
See application file for complete search history.

(56) References Cited

U.S. PATENT DOCUMENTS

| 7,579,010 | B2 | 8/2009 | Hunt | |
|---|---|---|---|---|
| 7,758,873 | B2 | 7/2010 | Hunt | |
| 7,780,967 | B2 | 8/2010 | Hunt | |
| 7,829,525 | B2 | 11/2010 | Frevert | |
| 8,216,591 | B2 | 7/2012 | Hunt | |
| 8,501,196 | B2 | 8/2013 | Hunt | |
| 8,617,568 | B2 | 12/2013 | Jung | |
| 8,632,785 | B2 | 1/2014 | Hunt | |
| 9,220,780 | B2 | 12/2015 | Jung | |
| 9,302,008 | B2 | 4/2016 | Hunt | |
| 9,340,587 | B2 | 5/2016 | Thompson | |
| 2007/0134199 | A1* | 6/2007 | Frevert | A61K 9/0019 424/85.4 |
| 2010/0330123 | A1 | 12/2010 | Thompson | |
| 2012/0107361 | A1 | 5/2012 | Thompson | |
| 2012/0302507 | A1 | 11/2012 | Ham | |
| 2014/0161783 | A1* | 6/2014 | Jung | A61K 9/0019 424/94.3 |
| 2016/0256532 | A1 | 9/2016 | Thompson | |

OTHER PUBLICATIONS

Kazuo et al, "Effectiveness of Licocaine/Prilocaine Combination Cream (EMLA® Cream) on Puncture such as with Injection Needle and Indication for Children", Prog. Med., 35: 1641-1647, (2015).
Kondo et al, "Analgesic Effect of Lidocaine Cream during the Injection of Botulinum a Toxin", Facial N Res Jpn, 31: 158-160, (2011)

\* cited by examiner

*Primary Examiner* — Rodney P Swartz
(74) *Attorney, Agent, or Firm* — DLA Piper LLP

(57) ABSTRACT

The present invention relates to a liquid formulation containing botulinum toxin and stabilizing agent, and preparation method therefor. A liquid formulation containing botulinum toxin and stabilizing agent according to the present invention be can be easily stored and distributed. It was proved a significant effect on the stabilization of botulinum toxin under suitable conditions according to the temperature and pH of the human body. Thus, it is expected that the pharmaceutical composition of the present invention will greatly contribute to the safe and convenient medical use of botulinum toxin.

13 Claims, 20 Drawing Sheets

[Figure 1]
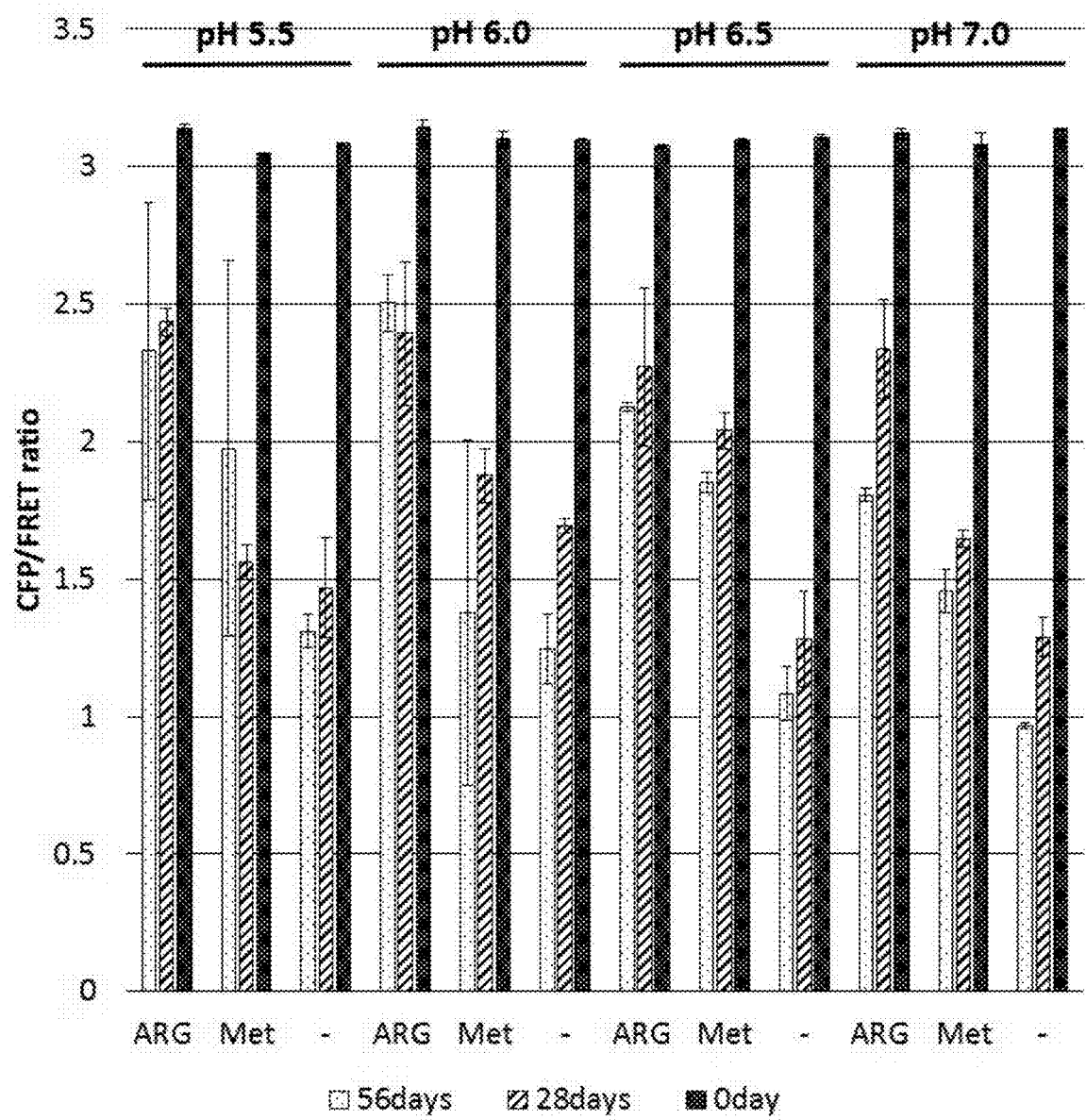

【Figure 2a】 pH6.0

[Graph showing BoNT/A Efficiency % vs Days at pH6.0, with three series: Arg50mM (squares), Met50mM (triangles), and Control (circles). Y-axis ranges from -20 to 120. X-axis from 0 to 60 days.]

━■━ Arg50mM  ━▲━ Met50mM  ━●━ Control

【Figure 2b】
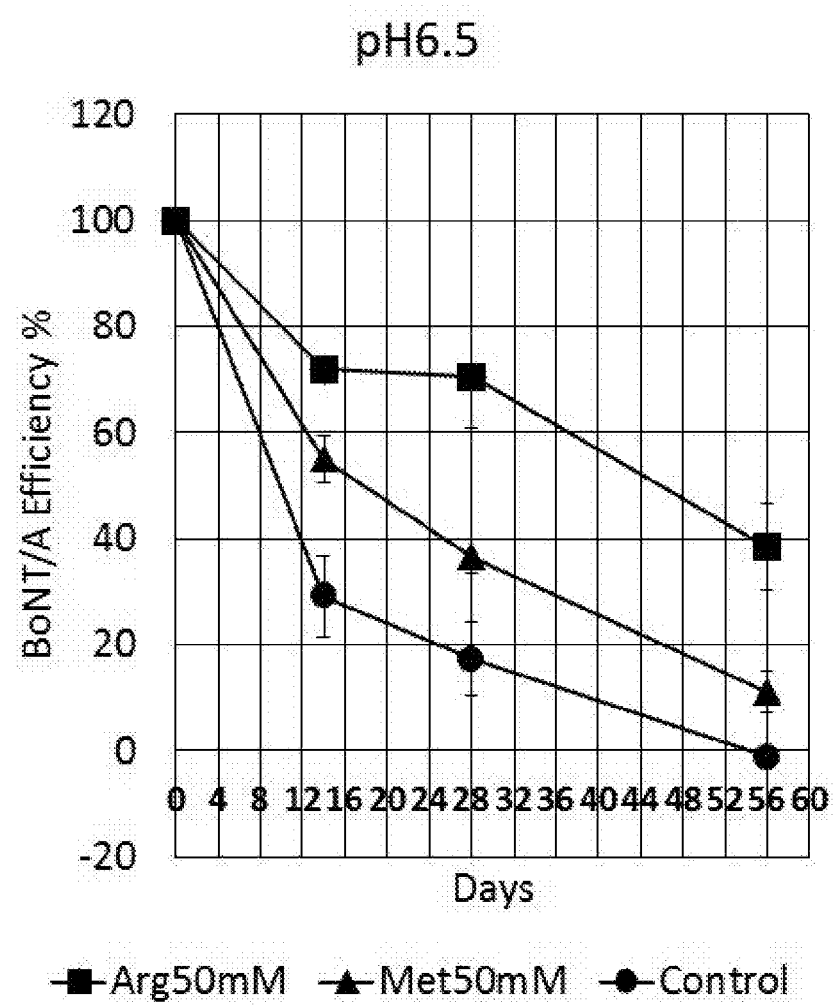

[Figure 2c]
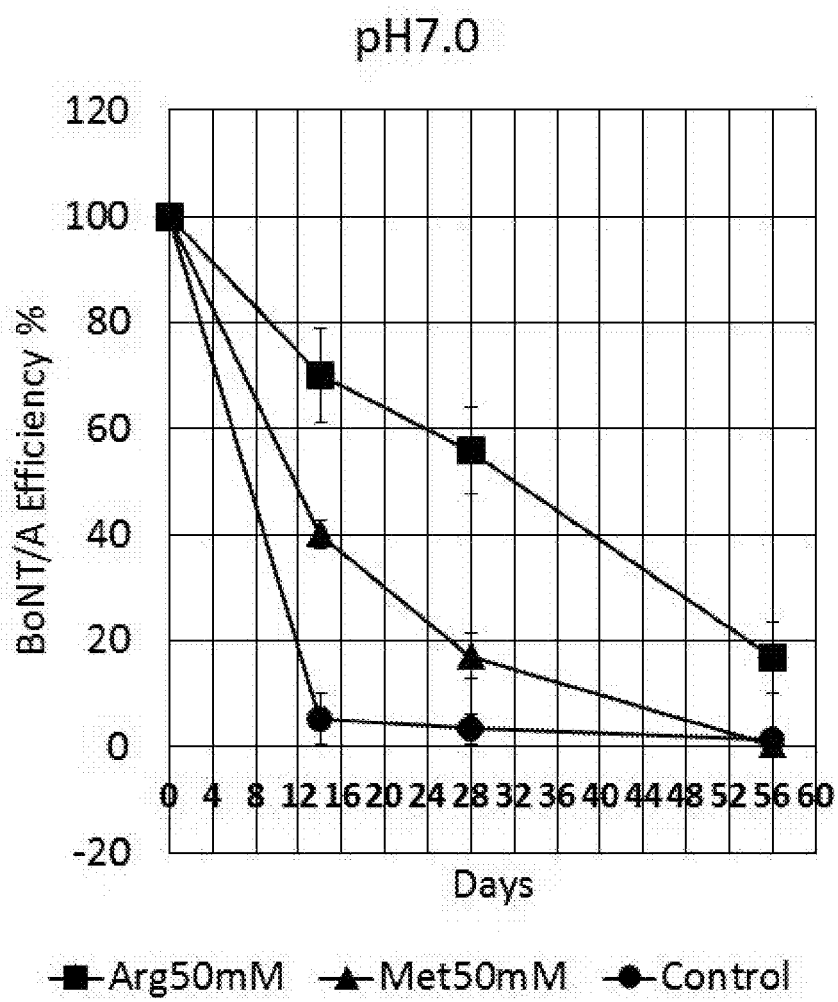

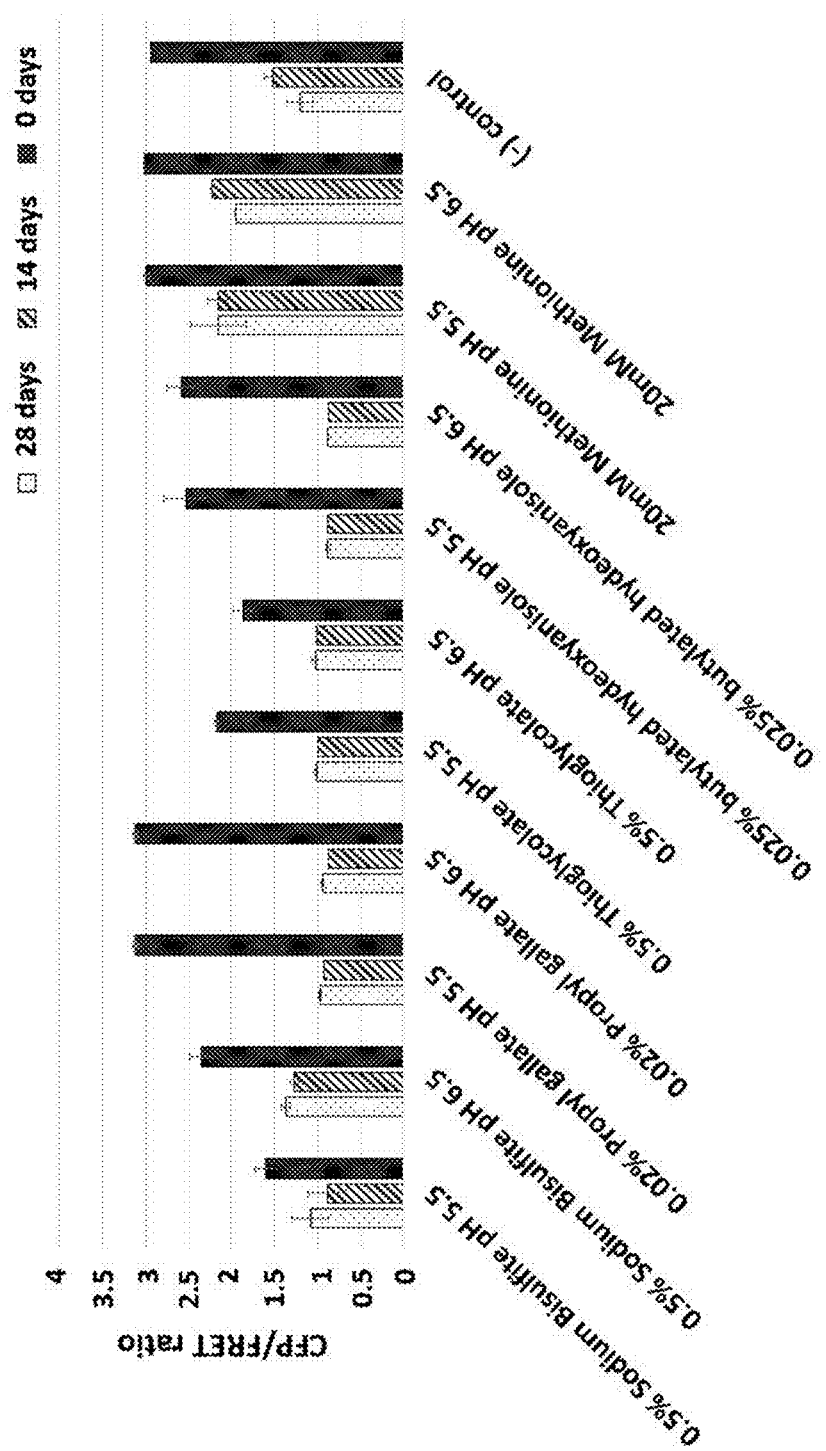
[Figure 3]

[Figure 4]
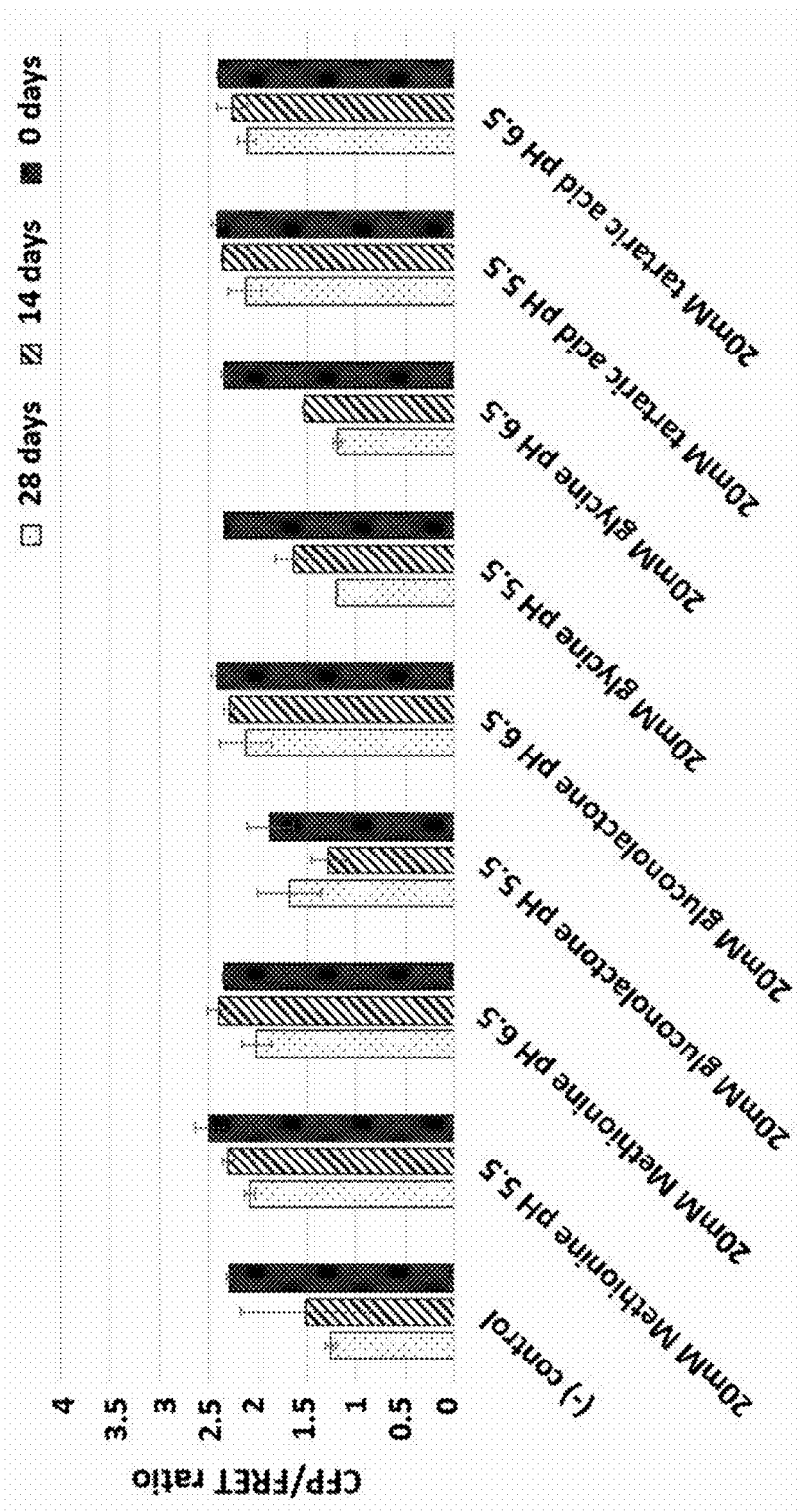

【Figure 5】
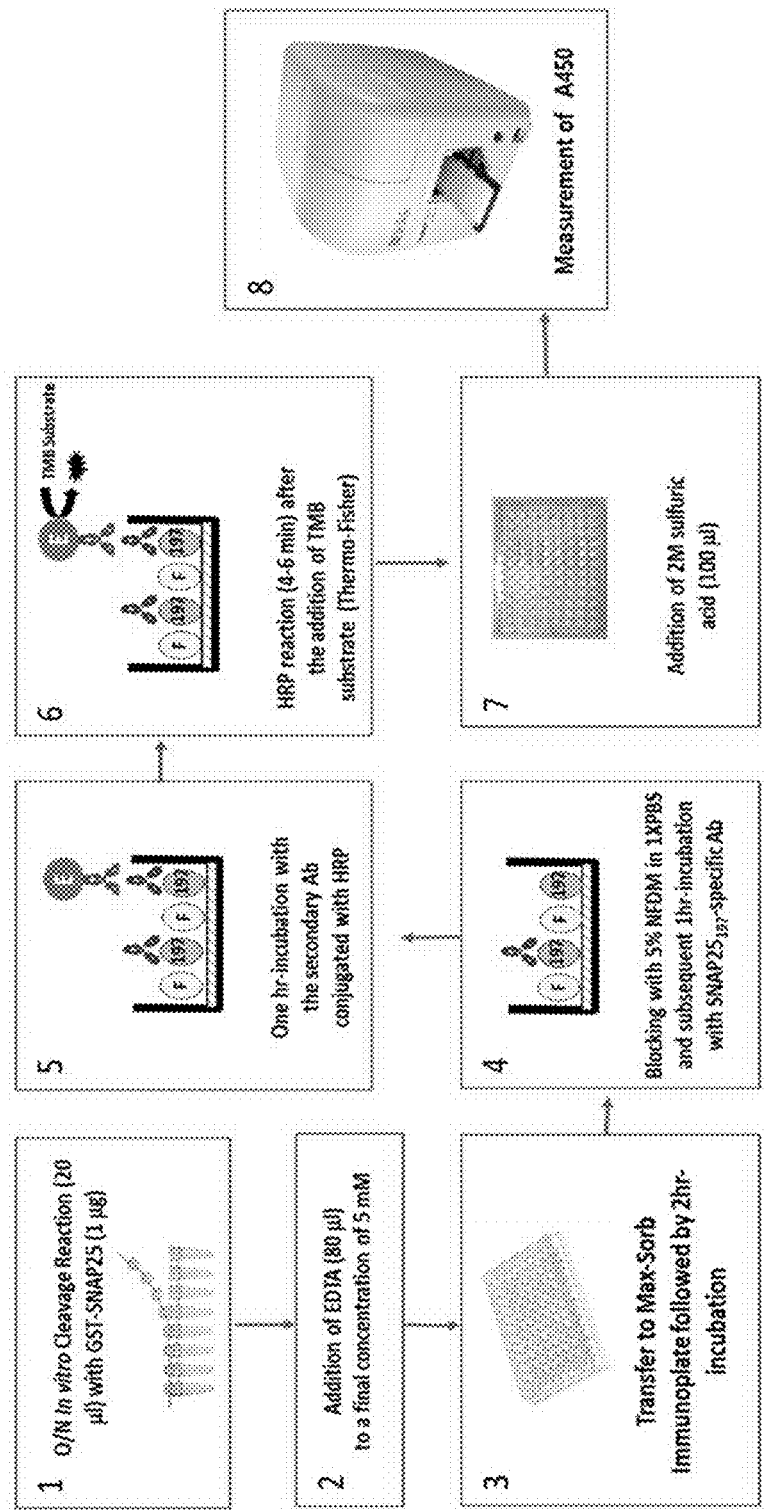

[Figure 6a]
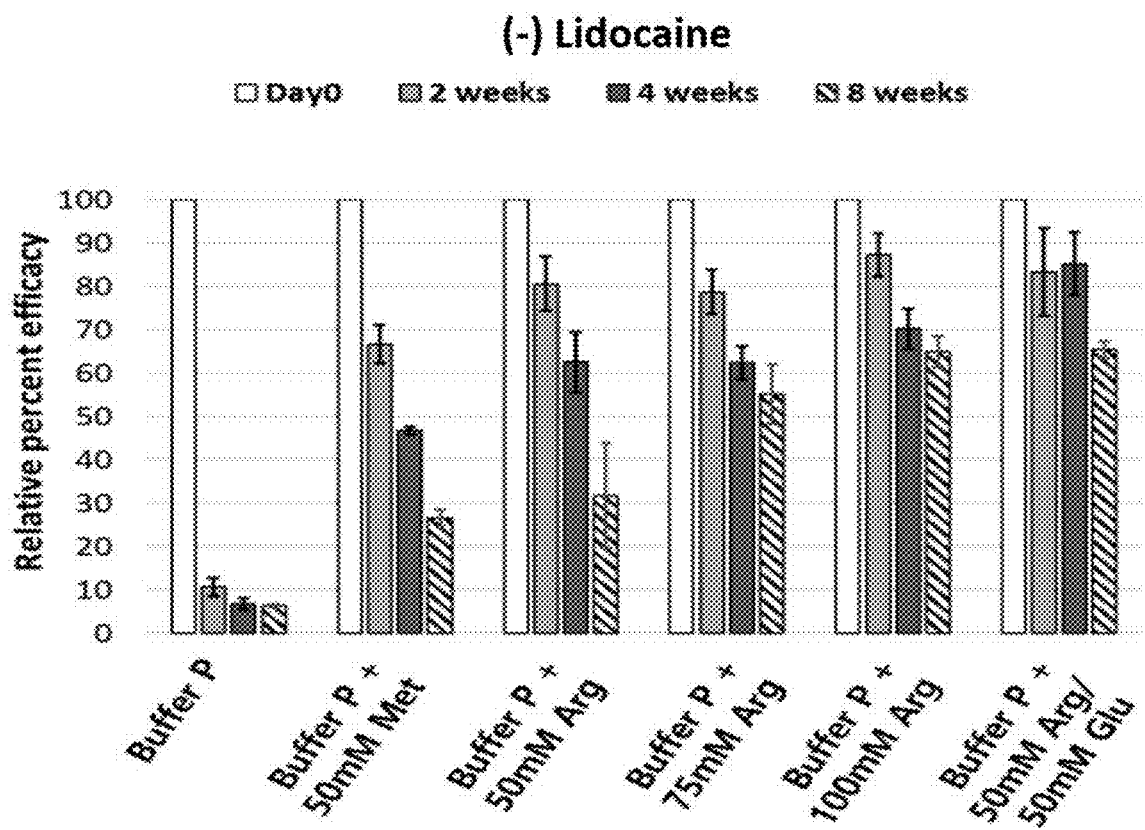

[Figure 6b]
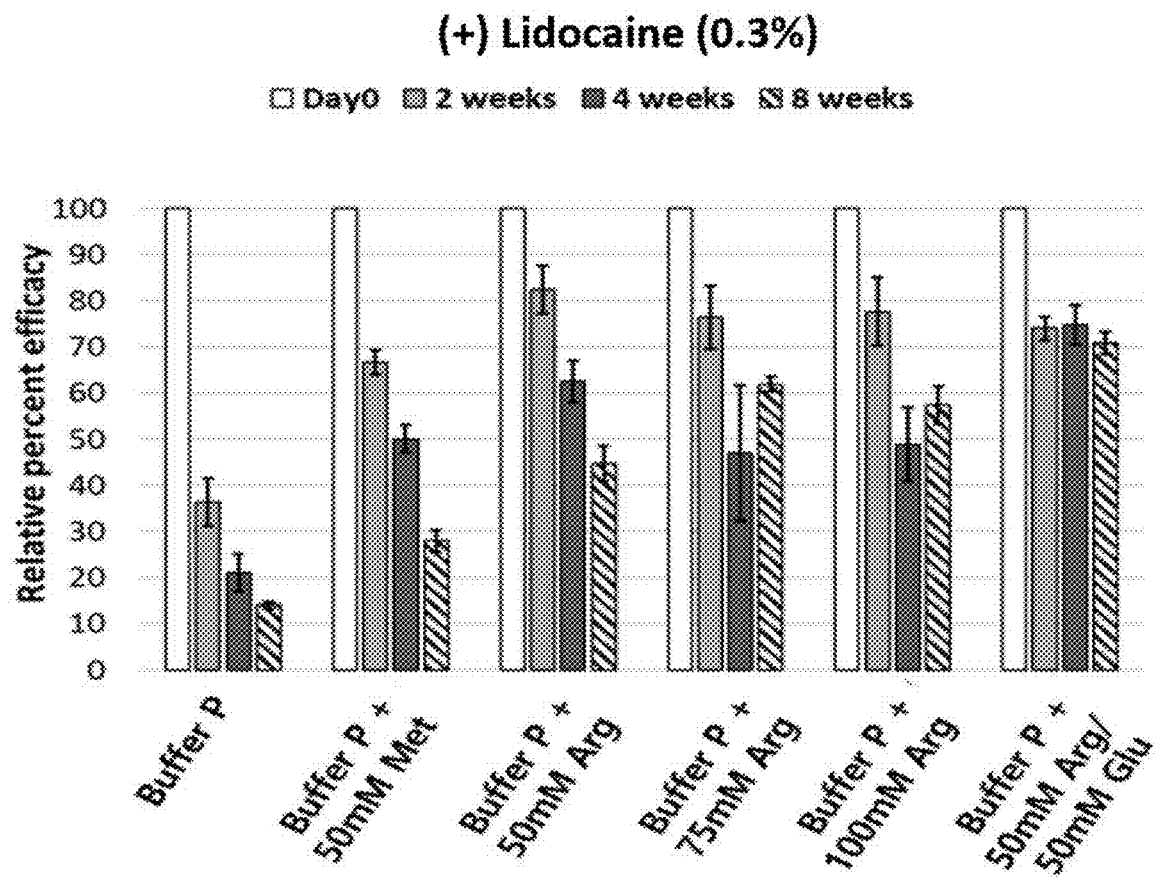

[Figure 7a]
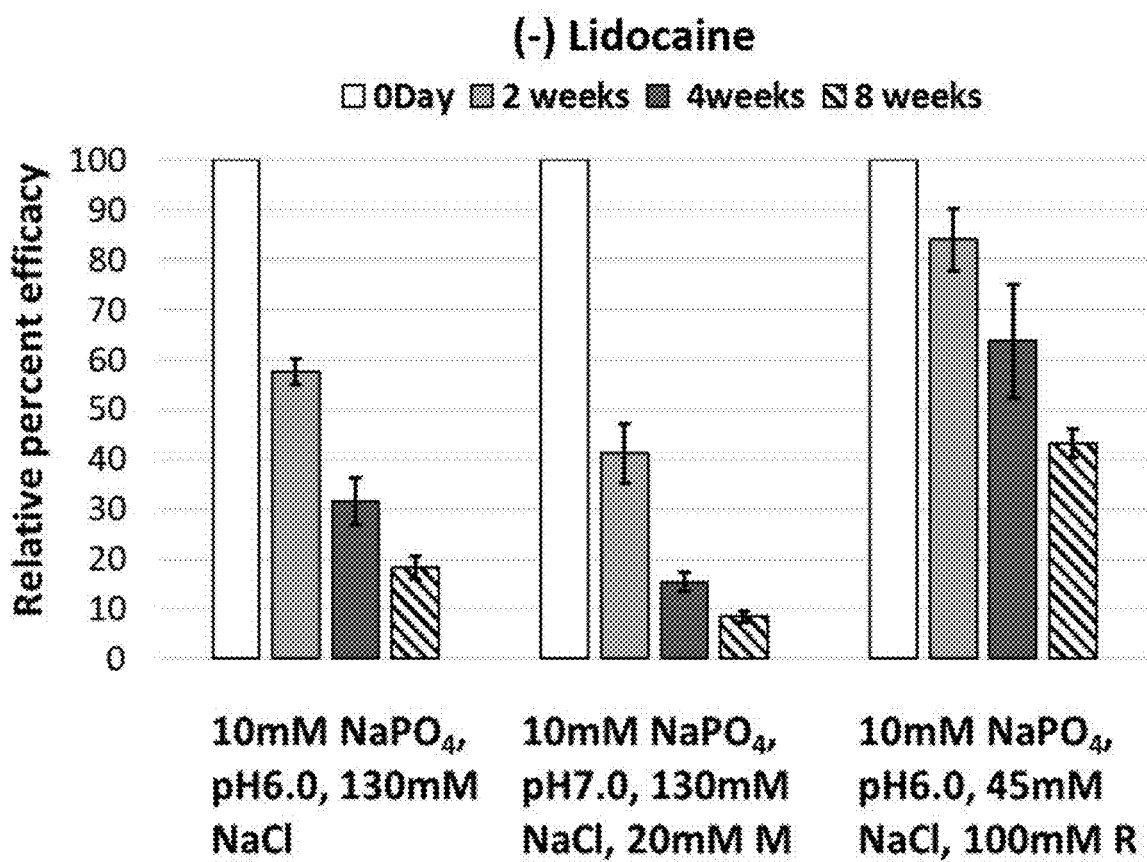

[Figure 7b]
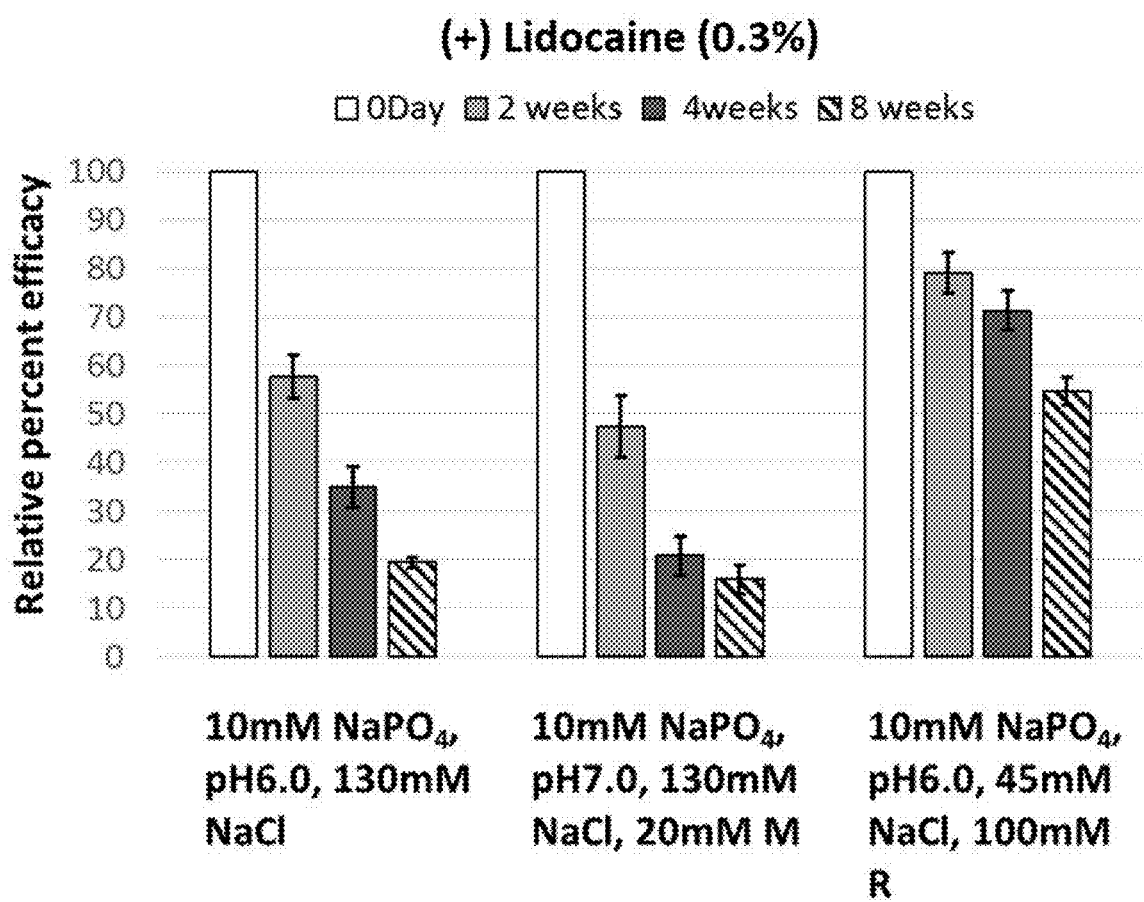

【Figure 8a】
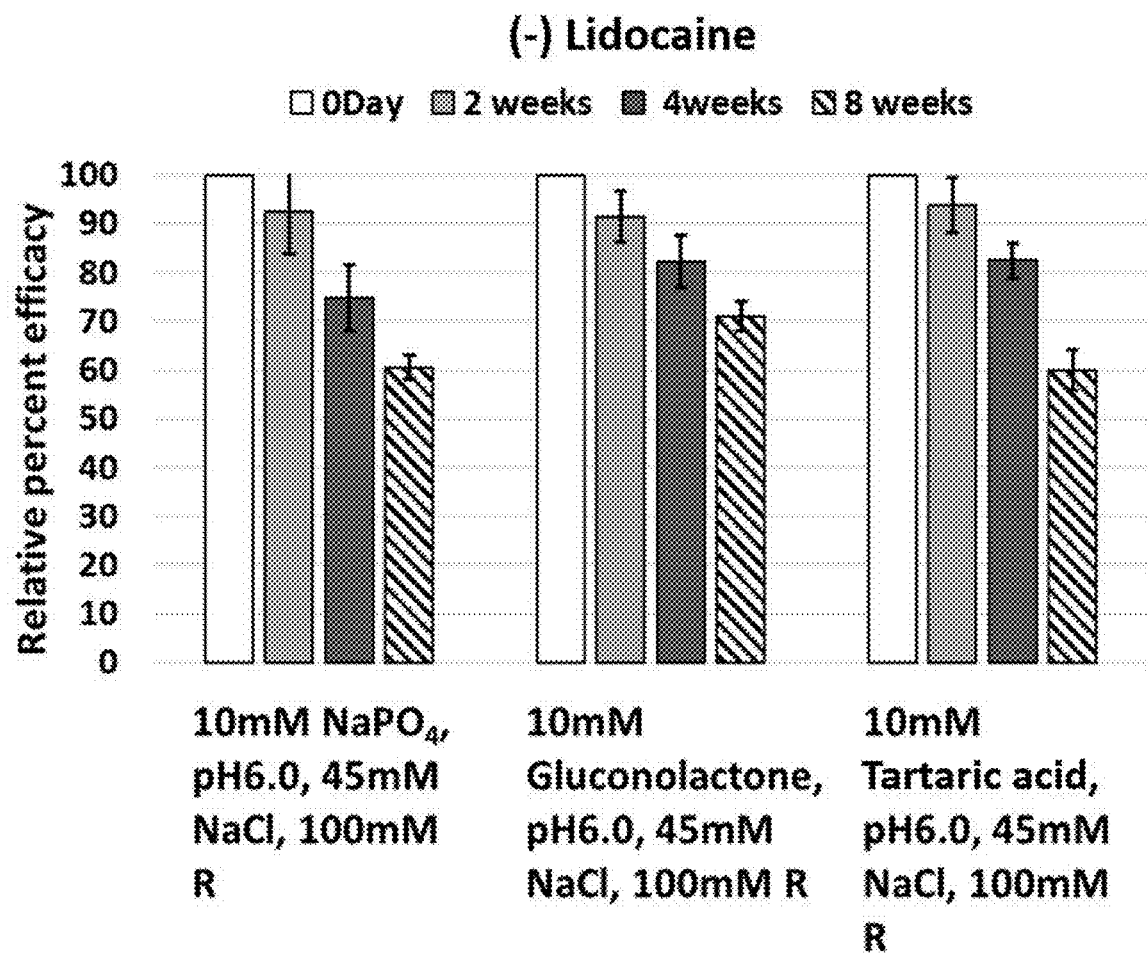

【Figure 8b】
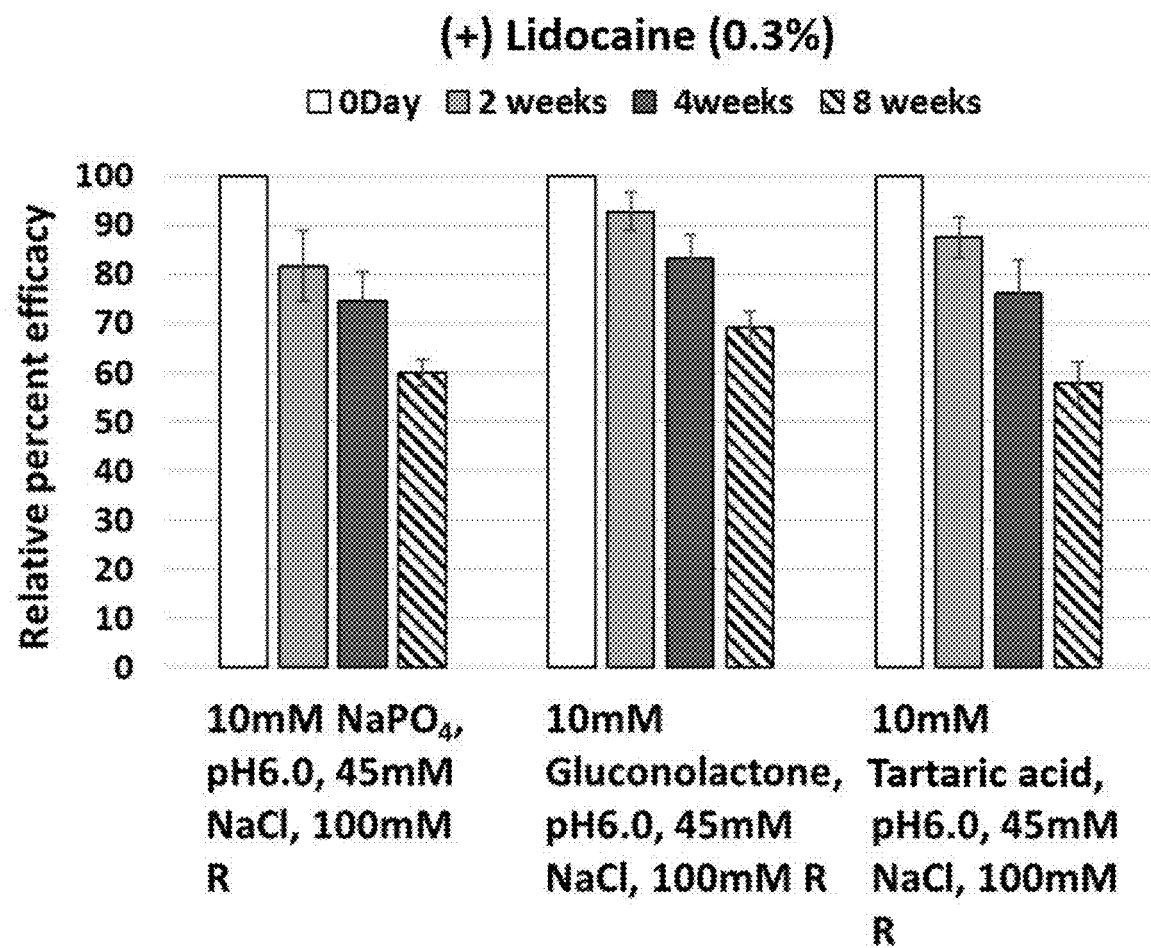

[Figure 9a]
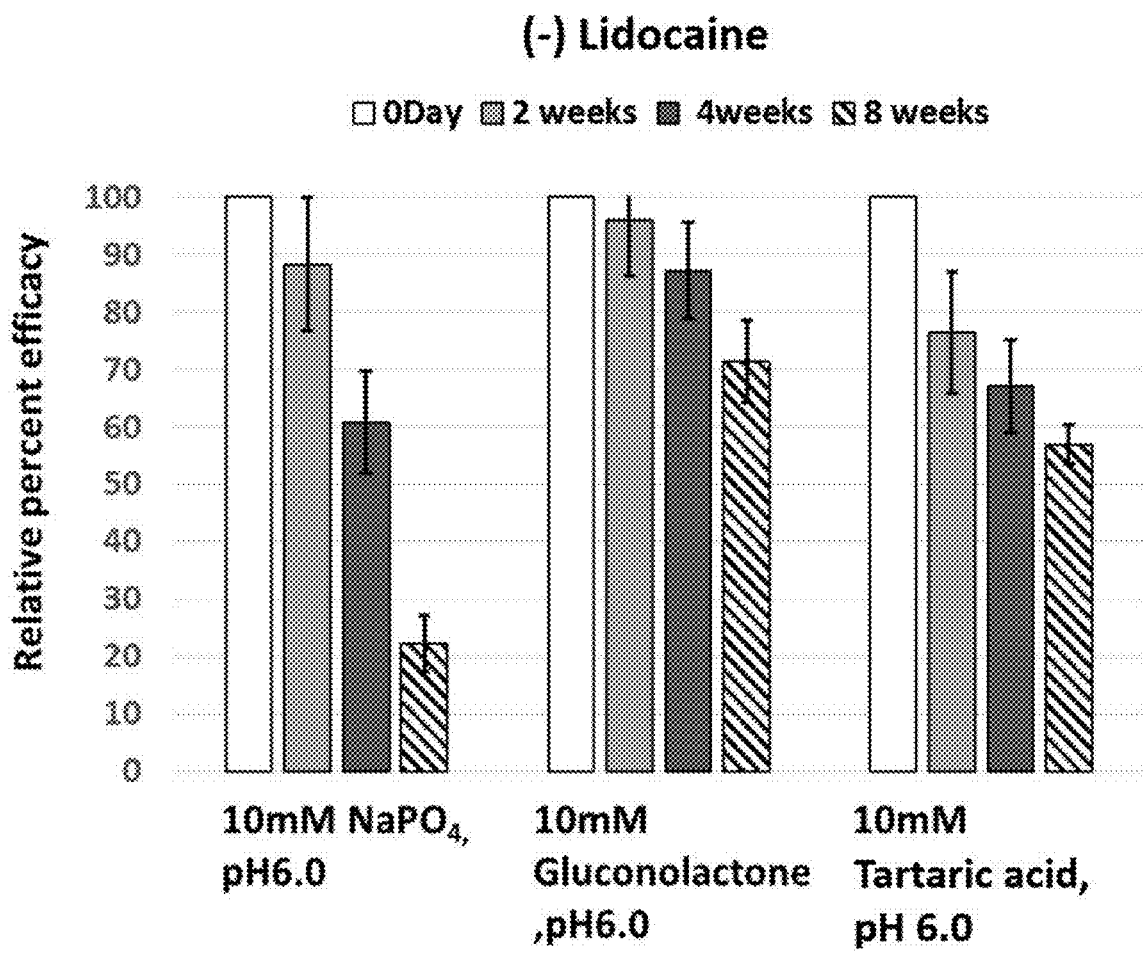

【Figure 9b】
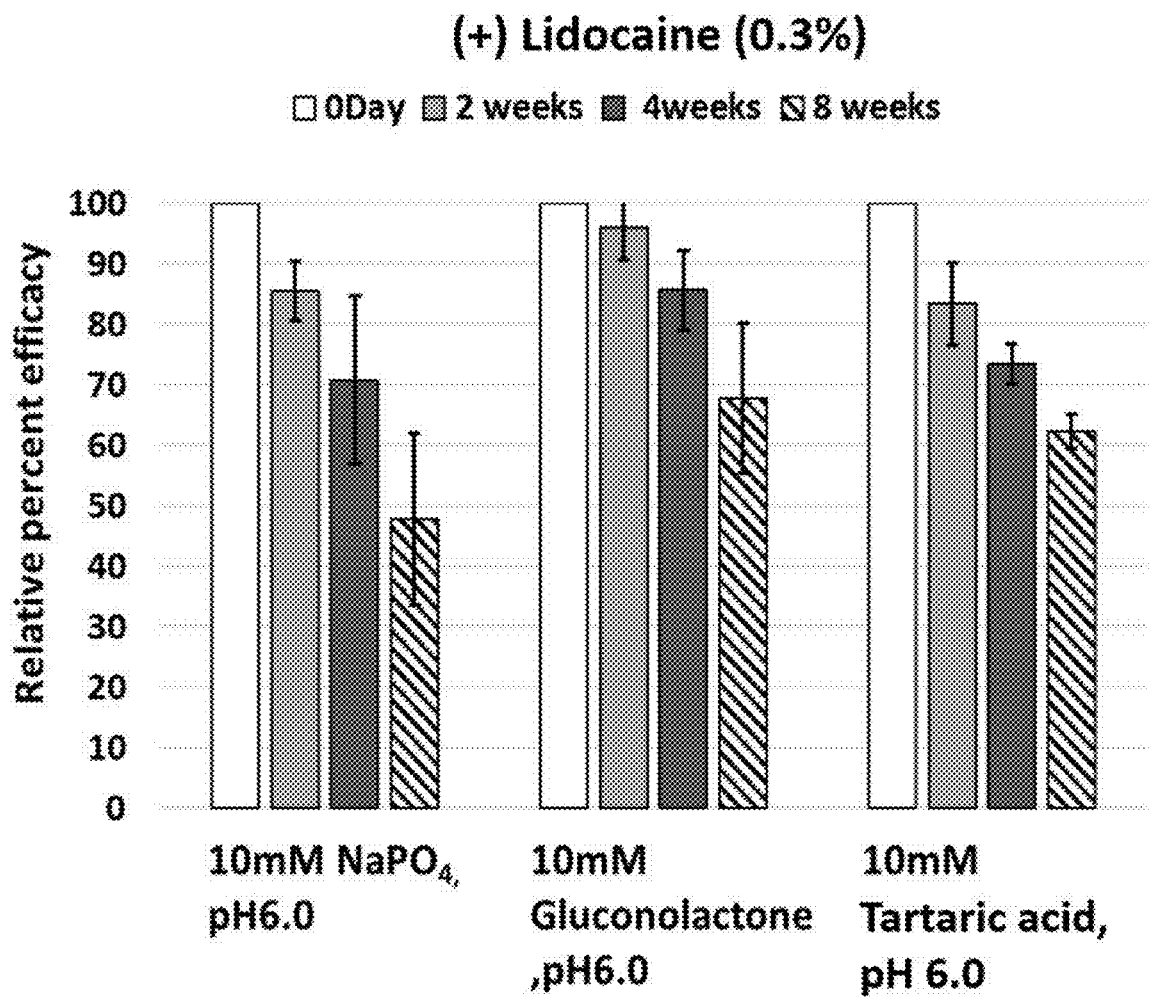

[Figure 10a]
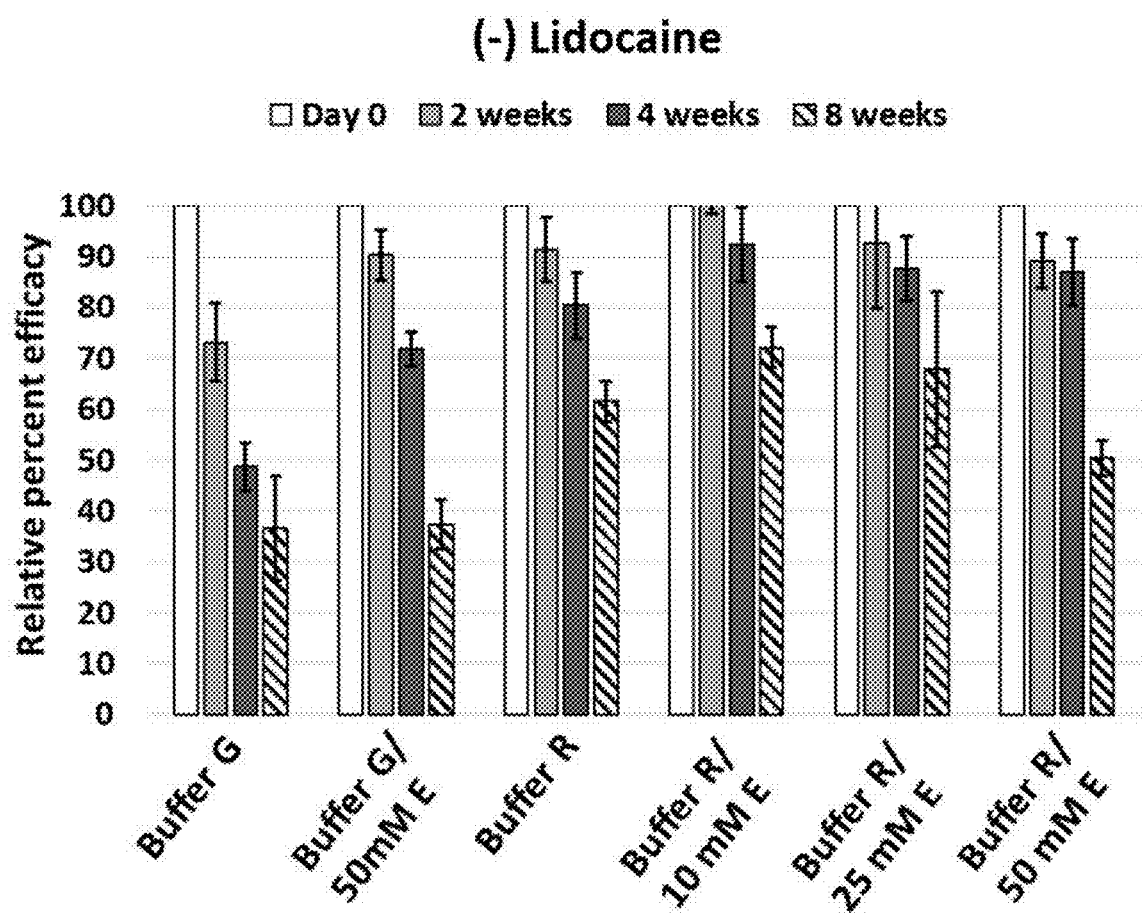

【Figure 10b】
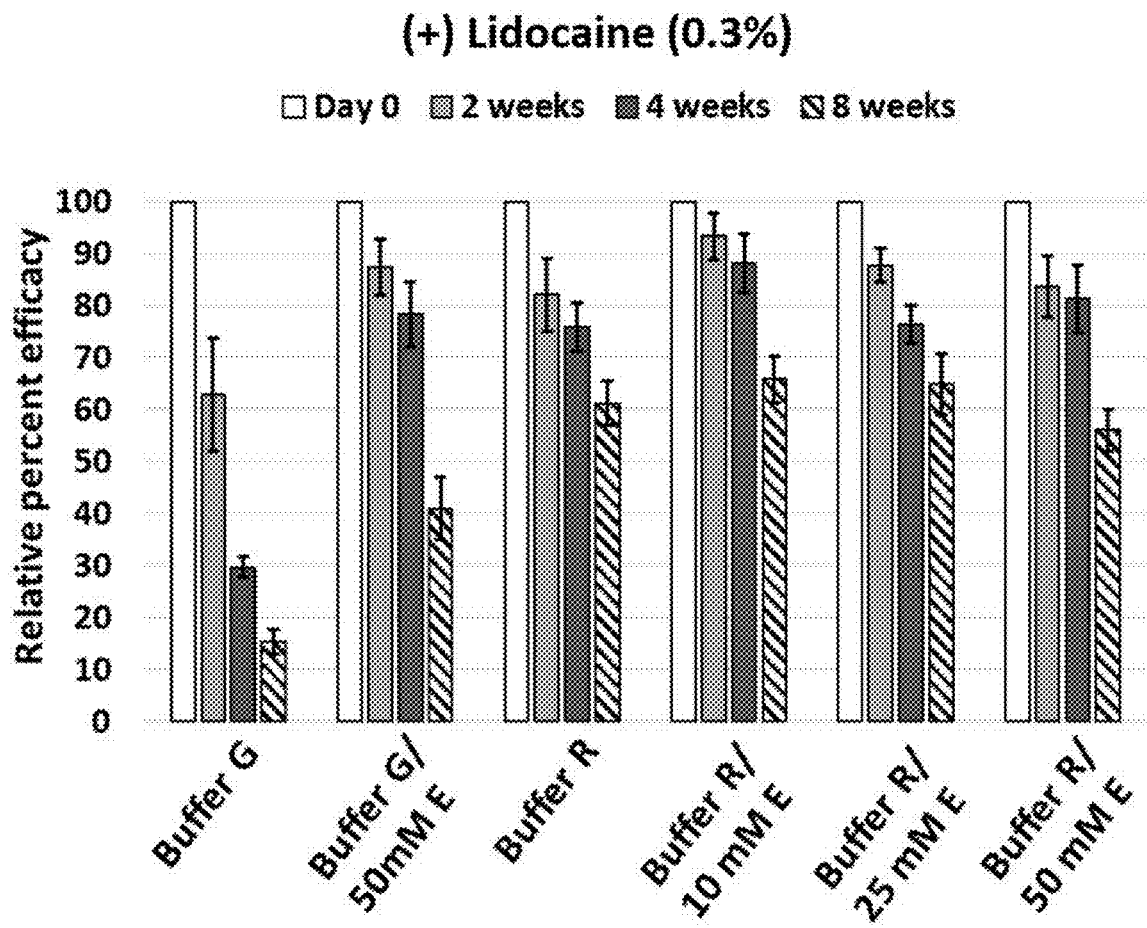

[Figure 11a]
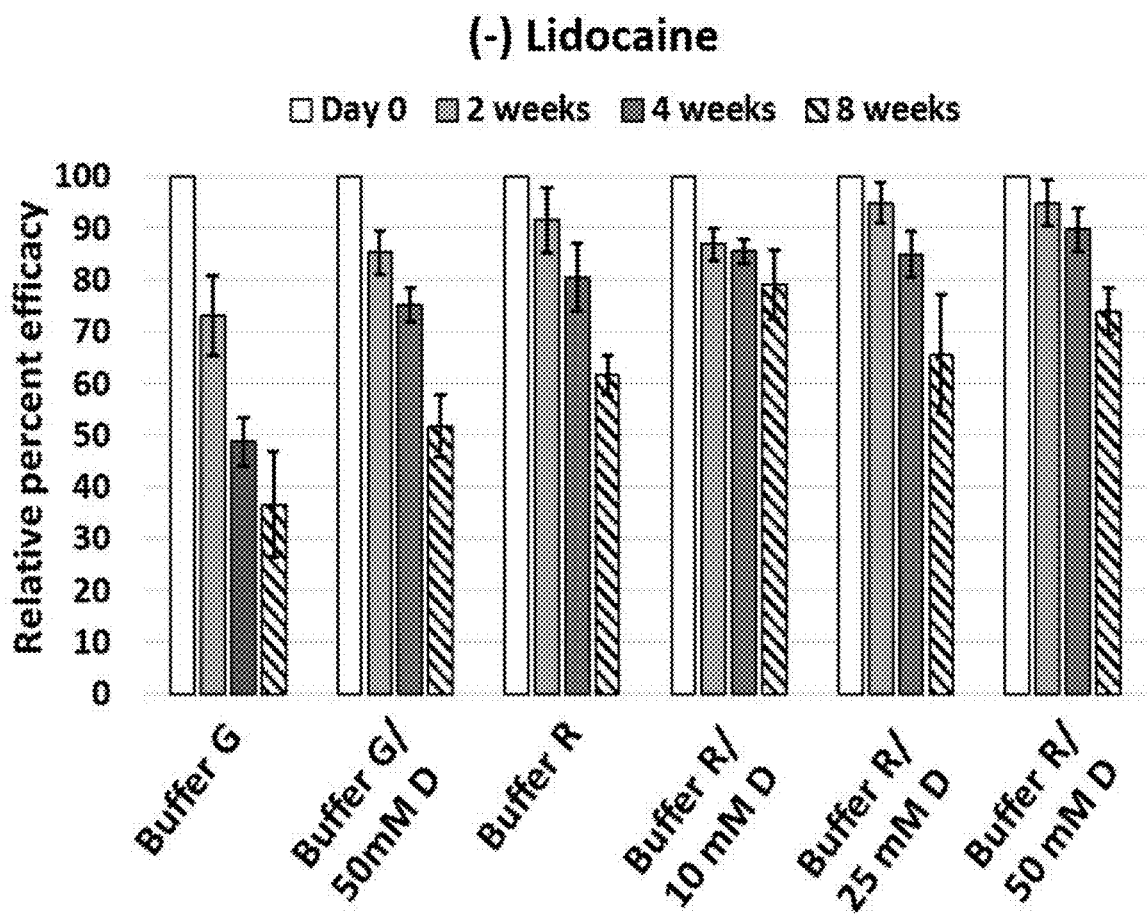

[Figure 11b]
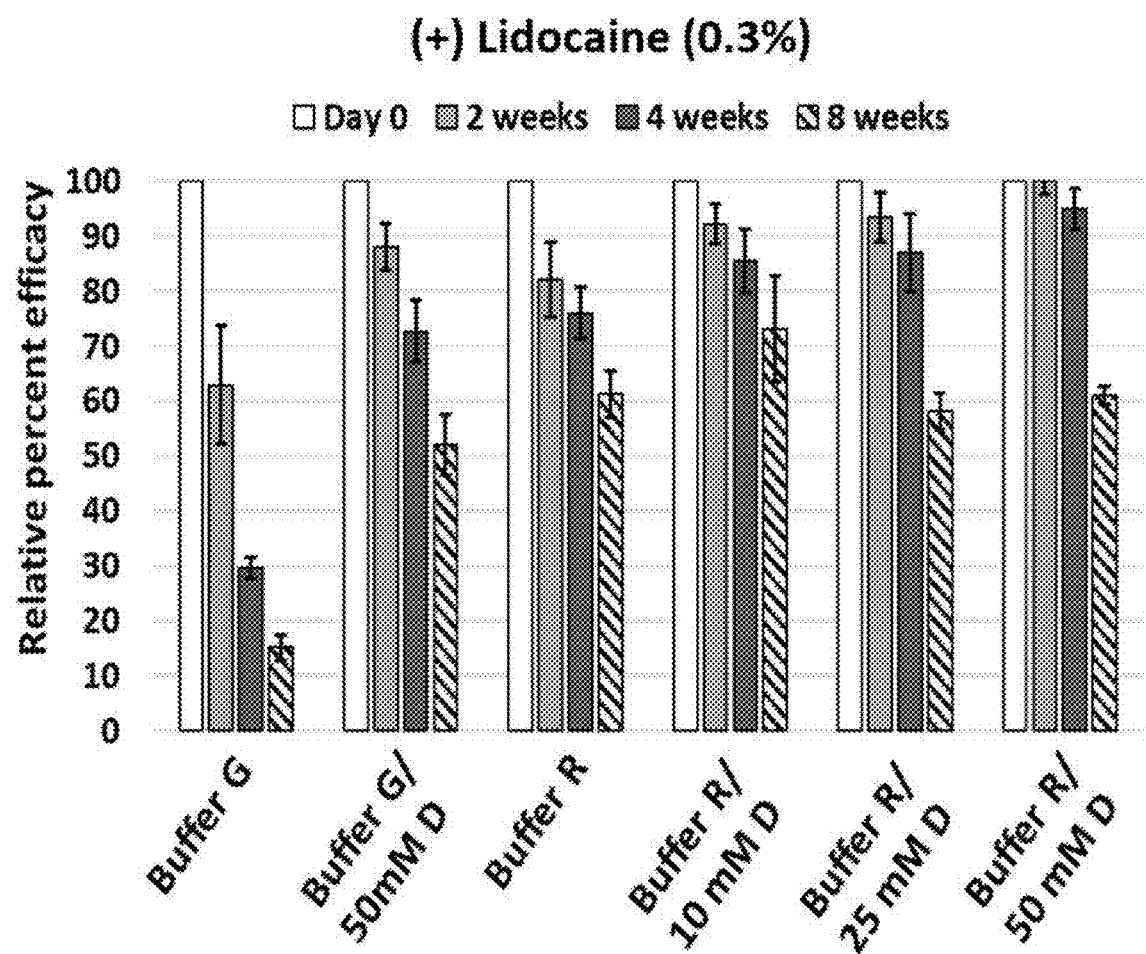

[Figure 12]
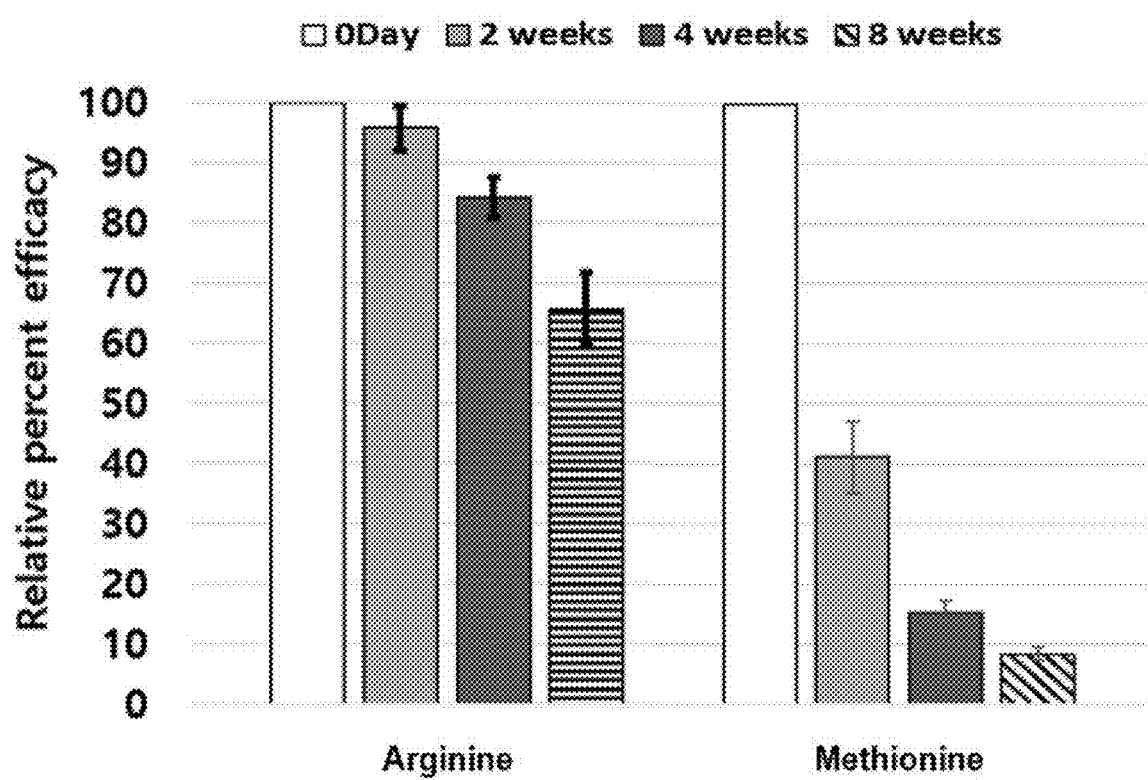

LIQUID FORMULATION CONTAINING BOTULINUM TOXIN AND STABILIZING AGENT, AND PREPARATION METHOD THEREFOR

TECHNICAL FIELD

The present invention relates to a liquid formulation containing botulinum toxin and stabilizing agent, and preparation method therefor.

BACKGROUND ART

A variety of *Clostridium* sp. strains which secrete toxins having neurotoxic effects have been discovered since the 1890s up to the present time, and the characterization of toxins that are secreted from these strains has been made over the past 70 years (Schant, E. J. et al., Microbiol. Rev., 56:80, 1992). Among these toxins, botulinum toxin inhibits the exocytosis of acetylcholine at the cholinergic presynapse of a neuromuscular junction in animals having neurological function to thereby cause asthenia. Thus, efforts have recently been made to use the neurotoxicity of botulinum toxin for cosmetic or therapeutic purposes. Technologies for using botulinum toxin for treatment of optic diseases (U.S. Pat. No. 6,265,379), pain (U.S. Pat. No. 6,113,915), various autonomic nerve disorders, including sweat gland disorders (U.S. Pat. No. 5,766,605), migraine headache pain (U.S. Pat. No. 5,714,468), post-operative pain and visceral pain (U.S. Pat. No. 6,464,986), psoriasis and dermatitis (U.S. Pat. No. 5,670,484), various cancers (U.S. Pat. Nos. 6,139,845 and 6,063,768), and neurogenic inflammation (U.S. Pat. No. 6,063,768), etc. have been proposed or attempted. However, botulinum toxin, a protein agent, has a problem in that it is not easy to formulate into pharmaceutical compositions and is also not easy to store, distribute and manage. This is attributable to the instability of the protein, and the problem is serious in the case of protein agents such as botulinum toxin, which are formulated into pharmaceutical compositions at a very low concentration. Botulinum toxin protein has the property of adhering to a solid surface, and for this reason, when the protein is injected into a container, a portion of the protein may adhere to the inner wall of the container to cause the loss of the active ingredient, and the protein may be easily oxidized or degraded into small fragments. For this reason, in order to prevent the denaturation of botulinum toxin to the greatest possible extent, botulinum toxin purified in a production process thereof is distributed as freeze-dried powder, which is diluted in a saline immediately before use in clinical applications and administered to patients in the form of liquid. However, in this case, there is also a problem in that medical accidents are highly likely to occur due to human errors such as a dilution factor error caused by the user or contamination of a dilution saline.

Therefore, it is urgently needed to develop stabilizers that can prevent protein denaturation even during the production and distribution of a liquid formulation of botulinum toxin.

In the prior art, albumin was actively used as a stabilizer to maintain the activity of botulinum toxin. However, due to the risk of cross infection and side effects of animal-derived components, the development of non-animal formulations has recently been required. In response to this requirement, US Patent Application Publication No. 2007-0134199 discloses a botulinum toxin composition comprising either glutamine and glutamic acid or asparagine and aspartic acid as amino acids, and Korean Patent No. 1087017 discloses a botulinum toxin composition comprising methionine as a stabilizer. However, these patent documents do not suggest remarkable effects under suitable conditions according to the temperature and pH of the human body.

Therefore, the present invention is directed to a liquid formulation containing botulinum toxin and stabilizing agent, and preparation method therefor. A pharmaceutical composition comprising botulinum toxin according to the present invention may contain arginine, glutamic acid, or aspartic acid as a stabilizer, or may contain gluconolactone buffer, or tartaric acid buffer as a stabilization buffer for botulinum toxin. AND it was proved a significant effect on the stabilization of botulinum toxin under suitable conditions according to the temperature and pH of the human body. Thus, it is expected that the pharmaceutical composition of the present invention will greatly contribute to the safe and convenient medical use of botulinum toxin.

DISCLOSURE

Technical Problem

The present invention has been made in order to solve the above-described problems occurring in the prior art, and it is an object of the present invention to provide a liquid formulation containing botulinum toxin and stabilizing agent, and preparation method therefor.

However, the technical object to be achieved by the present invention is not limited to the above-mentioned technical object, and other objects that are not mentioned above can be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise specified in the specification, all the scientific and technical terms used in the specification have the same meanings as commonly understood by those skilled in the technical field to which the present invention pertains.

In one embodiment of the present invention, "botulinum toxin" is a neurotoxic protein produced by the bacterium *Clostridium botulinum*. The genus *Clostridium* has more than 127 species, grouped according to their morphology and functions. The anaerobic, gram-positive bacteria

*Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The symptoms of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty in walking, swallowing, and speaking to paralysis of the respiratory muscles and death.

Botulinum toxin type A is known as the most lethal natural biological agent to man. About 50 picograms of a commercially available botulinum toxin type A (purified neurotoxin complex) is an LD50 (i.e., 1 unit). Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. One unit (U) of botulinum toxin is defined as the LD50 upon intraperitoneal injection into female Swiss Webster mice weighing 18 to 20 grams each.

Immunologically distinct 7 botulinum neurotoxins have been generally characterized as botulinum neurotoxin serotypes A, B, C1, D, E, F and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than botulinum toxin type B. Additionally, botulinum toxin type B has been determined to be non-toxic in primates at a dose of 480 U/kg which is about 12 times the primate LD50 for botulinum toxin type A. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least 3 steps. In the first step of the process, the toxin binds to the presynaptic membrane of the target neuron through a specific interaction between the heavy chain (the H chain or HC), and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, and an endosome containing the botulinum toxin is formed. The toxin then escapes the endosome into the cytoplasm of the cell. This step is thought to be mediated by the amino end segment of the heavy chain, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum toxin) then translocates through the endosomal membrane into the cytoplasm.

The last step of the mechanism of botulinum toxin activity appears to involve reduction of the disulfide bond joining the heavy chain and the light chain. The entire toxic activity of botulinum and tetanus toxins is contained in the light chain of the holotoxin; the light chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype C1 was originally thought to cleave syntaxin, but was found to cleave syntaxin and SNAP-25. Each of the botulinum toxins specifically cleaves a different bond, except type B (and tetanus toxin) which cleave the same bond. Each of these cleavages blocks the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989, a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about 3 months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and cleaving these proteins at different sites. For example, botulinum types A and E both cleave the 25 kDa synaptosomal associated protein (SNAP-25), but they target different amino acid sequences within this protein. Botulinum toxin types B, D, F and G act on vesicle-associated membrane protein (VAMP, also called synaptobrevin), with each serotype cleaving the protein at a different site. Finally, botulinum toxin type C1 appears to cleave both syntaxin and SNAP-25. These differences in mechanism of action may affect the relative potency and/or duration of action of the various botulinum toxin serotypes. Particularly, a substrate for a botulinum toxin can be found in a variety of different cell types.

The molecular weight of the botulinum toxin, for all seven of the known botulinum toxin serotypes, is about 150 kDa. Interestingly, the botulinum toxins are released by Clostridial bacterium as complexes comprising the 150 kDa botulinum toxin protein molecule along with associated non-toxin proteins. Thus, the botulinum toxin type A complex can be produced by Clostridial bacterium as 900 kDa, 500 kDa or 300 kDa forms. Botulinum toxin types B and C1 are apparently produced as only a 700 kDa or 500 kDa complex. Botulinum toxin type D is produced as 300 kDa or 500 kDa complexes. Finally, botulinum toxin types E and F are produced as only approximately 300 kDa complexes. The complexes (i.e. molecular weight greater than about 150 kDa) are believed to contain a non-toxin hemagglutinin proteins, a non-toxin, and non-toxic non-hemagglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kDa molecular weight) botulinum toxin complexes result in a slower rate of diffusion of the botulinum toxin away from a site of intramuscular injection of a botulinum toxin complex.

In vitro studies have indicated that botulinum toxin inhibits potassium cation-induced release of both acetylcholine and norepinephrine from primary cell cultures of brainstem tissue. In addition, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP, substance P, and glutamate. Thus, when adequate concentrations are used, the stimulus-evoked release of most neurotransmitters can be blocked by botulinum toxin.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can, therefore, be recovered from bacterial cultures in predominantly their active form. In contrast, botulinum toxin serotypes C1, D, and E are synthesized by nonproteolytic strains and are therefore typically inactivated when recovered from culture. Serotypes B and F are produced by both proteolytic and nonproteolytic strains, and thus can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Moreover, it is known that botulinum toxin type B has, upon intramuscular injection, a shorter duration of activity and is also less potent than botulinum toxin type A at the same dose level.

High-quality crystalline botulinum toxin type A can be produced from the Hall A strain of *Clostridium botulinum* with characteristics of $\geq 3 \times 10^7$ U/mg, an A260/A278 of less than 0.60 and a distinct pattern of banding on gel electrophoresis. The known Schantz process can be used to obtain crystalline botulinum toxin type A. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kDa molecular weight with a specific potency of $1-2 \times 10^8$ LD50 U/mg or greater; purified botulinum toxin type B with an approximately 156 kDa molecular weight with a specific potency of $1-2 \times 10^8$ LD50 U/mg or greater, and; purified botulinum toxin type F with an approximately 155 kDa molecular weight with a specific potency of $1-2 \times 10^7$ LD50 U/mg or greater.

Botulinum toxins and/or botulinum toxin complexes are commercially available from compound manufacturers known in the art, and pure botulinum toxin can also be used to prepare a pharmaceutical composition.

As with enzymes generally, the biological activities of the botulinum toxins (which are intracellular peptidases) are dependent, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the very low toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin should be stabilized with a suitable stabilizing agent. Thus, as disclosed in the present invention, the development of optimal stabilizer technology is necessary to control the in vivo release of botulinum toxin to a slow release form.

It has been reported that botulinum toxin type A has been used in clinical settings as follows:

The usual duration of an intramuscular injection of botulinum toxin administered in vivo is typically about 3 to 4 months. However, in some cases, botulinum toxin subtype A can have an efficacy for up to 12 months (*European J. Neurology* 6 (Supp 4): S111-S1150:1999), and in some circumstances for as long as 27 months, when used to treat glands, such as in the treatment of hyperhydrosis.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

A botulinum toxin has also been proposed for or has been used to treat skin bone and tendon wounds (U.S. Pat. No. 6,447,787); intrathecal pain (see U.S. Pat. No. 6,113,915); various autonomic nerve disorders, including sweat gland disorders (see e.g. U.S. Pat. No. 5,766,605 and Goldman (2000), Aesthetic Plastic Surgery July-August 24(4):280-282); tension headache (U.S. Pat. No. 6,458,365); migraine headache (U.S. Pat. No. 5,714,468); post-operative pain and visceral pain (U.S. Pat. No. 6,464,986); hair growth and hair retention (U.S. Pat. No. 6,299,893); psoriasis and dermatitis (U.S. Pat. No. 5,670,484); injured muscles (U.S. Pat. No. 6,423,319); various cancers (U.S. Pat. Nos. 6,139,845 and 6,063,768), smooth muscle disorders (U.S. Pat. No. 5,437,291); nerve entrapment syndromes (US Patent Application 2003-0224019); acne (WO 03/011333); neurogenic inflammation (U.S. Pat. No. 6,063,768); optic disorders (see U.S. Pat. No. 6,265,379); pancreatic disorders (see U.S. Pat. Nos. 6,143,306 and 6,261,572); prostate disorders, including prostatic hyperplasia, prostate cancer and urinary incontinence (see U.S. Pat. Nos. 6,365,164 and 6,667,041 and Doggweiler R., et al *Botulinum toxin type A causes diffuse and highly selective atrophy of rat prostate*, Neurourol Urodyn 1998; 17(4):363); fibromyalgia (U.S. Pat. No. 6,623,742), and *piriformis* muscle syndrome (see Childers et al. (2002), American Journal of Physical Medicine & Rehabilitation, 81:751-759).

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord. Additionally, it has been disclosed that targeted botulinum toxins (i.e. with a non-native binding moiety) can be used to treat various conditions (see WO 96/33273; WO 99/17806; WO 98/07864; WO 00/57897; WO 01/21213; WO 00/10598).

In addition, a botulinum toxin has been injected into the pectoral muscle to control pectoral spasm (Senior M., Botox and the management of pectoral spasm after subpectoral implant insertion, Plastic and Recon Surg, July 2000, 224-225). Controlled release toxin implants are known (see U.S. Pat. Nos. 6,306,423 and 6,312,708) as is transdermal botulinum toxin administration (U.S. patent application Ser. No. 10/194,805). It is known that a botulinum toxin can be used to: weaken the chewing or biting muscle of the mouth so that self inflicted wounds and resulting ulcers can be healed (Payne M., et al, Botulinum toxin as a novel treatment for self mutilation in Lesch-Nyhan syndrome, Ann Neurol 2002 September; 52 (3 Supp 1):S157); permit healing of benign cystic lesions or tumors (Blugerman G., et al., Multiple eccrine hidrocystomas: A new therapeutic option with botulinum toxin, Dermatol Surg 2003 May; 29(5):557-9); treat anal fissure (Jost W., Ten years' experience with botulinum toxin in anal fissure, Int J Colorectal Dis 2002 September; 17(5):298-302); and treat certain types of atopic dermatitis (Heckmann M., et al., Botulinum toxin type A injection in the treatment of lichen simplex: An open pilot study, J Am Acad Dermatol 2002 April; 46(4):617-9).

Additionally, a botulinum toxin may have the effect of reducing induced inflammatory pain in a rat formalin model (Aoki K., et al, Mechanisms of the antinociceptive effect of subcutaneous Botox: Inhibition of peripheral and central nociceptive processing, Cephalalgia 2003 September; 23(7):649). Furthermore, it has been reported that botulinum toxin nerve blockage can cause a reduction of epidermal thickness (Li Y, et al., Sensory and motor denervation influences epidermal thickness in rat foot glabrous skin, Exp Neurol 1997; 147:452-462). Finally, it is known to administer a botulinum toxin to the foot to treat excessive foot sweating (Katsambas A., et al., Cutaneous diseases of the foot: Unapproved treatments, Clin Dermatol 2002 November-December; 20(6):689-699; Sevim, S., et al., Botulinum toxin-A therapy for palmar and plantar hyperhidrosis, Acta Neurol Belg 2002 December; 102(4):167-70), spastic toes (Suputtitada, A., Local botulinum toxin type A injections in the treatment of spastic toes, Am J Phys Med Rehabil 2002 October; 81(10):770-5), idiopathic toe walking (Tacks, L., et al., Idiopathic toe walking: Treatment with botulinum toxin A injection, Dev Med Child Neurol 2002; 44(Suppl 91):6), and foot dystonia (Rogers J., et al., Injections of botulinum toxin A in foot dystonia, Neurology 1993 April; 43(4 Suppl 2)).

Tetanus toxin, as well as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight: about 50 kDa) covalently bound by a single disulfide bond to a heavy chain (molecular weight: about 100 kDa). Hence, the molecular weight of tetanus toxin and of each of the 7 botulinum toxins (non-complexed) is about 150 kDa. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for ganglioside receptors on the surface of presynaptic cholinergic neurons. Receptor-mediated endocytosis of tetanus toxin in peripheral cholinergic neurons results in retrograde axonal transport, blocking the release of inhibitory neurotransmitters from central synapses, and causing a spastic paralysis. Contrarily, it has been believed that receptor-mediated endocytosis of botulinum toxin in peripheral cholinergic neurons hardly results in retrograde transport, inhibition of acetylcholine exocytosis from the central synapses, and a flaccid paralysis. However, very recent report has suggested that botulinum toxin also can undergo retrograde transport along axons and possibly inhibit the release of acetylcholine in central synapse (Bomba-Warczak et al., Interneuronal Transfer and Distal Action of Tetanus Toxin and Botulinum Neurotoxins A and D in Central Neurons, Cell Reports, 2016 August; 16, 1974-1987).

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains (Binz T. et al., The Complete Sequence of Botulinum Neurotoxin Type A and Comparison with Other Clostridial Neurotoxins, J Biological Chemistry 265 (16); 9153-9158:1990).

In one embodiment of the present invention, "acetylcholine" is an ester of choline and acetic acid, which is the first known neurotransmitter. It is distributed throughout neurons, and has a chemical formula of $C_7H_{16}NO_2$ and a molecular weight of 146.21 kDa.

Typically, only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, specifically by the large pyramidal cells of the motor cortex, several different neurons in the basal ganglia, the motor neurons that innervate the skeletal muscles, the preganglionic neurons of the autonomic nervous system (both sympathetic and parasympathetic), the bag 1 fibers of the muscle spindle fiber, the postganglionic neurons of the parasympathetic nervous system, and some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances, acetylcholine has an excitatory effect. However, acetylcholine is known to have inhibitory effects at some of the peripheral parasympathetic nerve endings (for example, inhibition of heart rate by the vagal nerve).

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, when the denervated cells are permeabilized (as by electroporation) or directly injected with the toxin. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

In one embodiment of the present invention, the term "stabilizing agent" or "stabilizer" means any additive that is added to increase the stability of the active ingredient and prevent the active ingredient from being oxidized, crystallized, and is not particularly limited as long as it is pharmaceutically acceptable. An evaluation of the stabilizing effect of the stabilizer can be performed without limiting the temperature, but it is understood that the stabilizing effect is maintained for a long period at a lower temperature usually then a high temperature. Therefore, evaluation of long-term stabilization efficacy at low temperature can be replaced by "acceleration test" which is performed at a high temperature for a short time. For example, the result evaluated the stabilization effect of a specific stabilizer at 37° C. for 9 days, was the same at the result at 4° C. for 3 months, and the result evaluated the stabilization effect of a specific stabilizer at 37° C. for 74 days, was the same at the result at 24° C. for 24 months (iso-inc.com/medical-package-testing/accelerated-aging.html).

In the present invention, the stabilizer is added to preserve or maintain the biological activity of the Clostridial-type neurotoxin protein comprising the botulinum toxin, and preferably is selected from arginine, methionine, aspartic acid, glutamic acid, gluconolactone, tartaric acid, or sodium hyposulphate, and more preferably arginine, aspartic acid, or glutamic acid, but is not limited thereto.

In one embodiment of the present invention, the term "stabilization buffer" or "stabilization buffering agent" means both a stabilizer and an effect as a buffer. It can be prepared by adding a substance having stabilizing effect to a general buffer, a stabilizing synergic effect can be expected including additional stabilizers. In the present invention, the stabilization buffer is preferably gluconolactone buffer, or tartaric acid buffer, but is not limited thereto.

In one embodiment of the present invention, "arginine" is a kind of basic amino acid, has a molecular formula of $C_6H_{14}N_4O_2$ and a molecular weight of 174.21, and is water-soluble. This residue is abbreviated as 'Arg' and is denoted by the single letter 'R'. It was first isolated from seedlings of lupin (a kind of bean) by M.J.S. Schulze and E. Steiger. Arginine was named because the nitrate thereof is argent. L-arginine is present as one of amino acids constituting a protein, and is found in the protein protamine present in the sperm of fish. About 70% of constituent amino acids in herrings and salmons are arginines. In plant seeds, arginine is present in a free state. Arginine residues are strongly basic due to their guanidine group. It can be quantified because it shows its peculiar red color when it is reacted with α-naphthol and alkaline hypochlorite. In in vivo metabolic pathways, arginine is a component of the ornithine pathway discovered by H. A. Krebs et al., and is cleaved to urea and ornithine by the action of arginase. Arginine is produced from citrulline and asparaginic acid. It is a non-essential amino acid in adults, but is an essential amino acid in infants. It provides protection against the toxicity of ammonia or large amounts of amino acids. Arginase is present in the brain and controls the amount of arginine that is a precursor of γ-guanidinobutyric acid. In invertebrate animals, arginine present in the form of arginine phosphate, plays an important role in muscular contraction with the phosphagen, and is also widely present as a precursor of a special guanidine base (magmatin, octopine).

In one embodiment of the present invention, "glutamic acid" is a kind of amino acid, and is also referred to as "glutamic acid", and is represented by the residues "Glu" or "E", and the molecular formula is $C_5H_9NO_4$. It was first found in the hydrolyzate of wheat gluten. It is one of the most abundant protein amino acids, especially in wheat gliadin, containing 43.7% of the protein. It is possible to separate hydrochloride by saturated hydrogen chloride from hydrolyzate of protein of wheat, soybean, etc.

In one embodiment of the present invention, "aspartic acid" is a kind of amino acid, and is also referred to as "aspartic acid", and is represented by the residues "Asp" or "D", and the molecular formula is $C_4H_7NO_4$. It is one of the amino acids constituting the protein. It is an acidic amino acid having two carboxyl groups (—COOH) in the molecule, and is naturally classified as a non-essential amino acid. Like glutamine, it is known to play a central role in the transamination of amino acids in vivo.

In one embodiment of the present invention, "gluconolactone" means a white crystal or a crystalline powder which has no or little odor, exhibits a sweet taste at first and a slightly sour taste later. The formula is $C_6H_{10}O_6$. It is a synthetic baking agent that dissolves well in water and slightly soluble in ethanol, but does not dissolve in ether. The aqueous solution is slowly hydrolyzed to form an equilibrium state among gluconic acid, δ-lactone, and γ-lactone, and the higher the temperature and pH, the faster the hydrolysis occurs. After about 2 hours at room temperature of 25° C., it is completely hydrolyzed to a solution of 55-60% gluconic acid and 40-50% lactone. Although the glucono-δ-lactone is not an acid, it is hydrolyzed to dissolve in water to exhibit acidity. Therefore, it is preferable to use it as an acidity modifier for swelling agent, and even if it is mixed with sodium hydrogencarbonate (sodium bicarbonate), no reaction occurs. In addition, since hydrolysis occurs slowly, when used as an acidity modifier for a swelling agent, it can react with sodium hydrogencarbonate to make a product having a very fine texture. Also, it has antioxidant ability because it forms a complex with metal. Although it is not an acid, it is used for lowering the pH of softened product because the aqueous solution shows acidity by heating.

In one embodiment of the present invention, "tartaric acid" is an organic compound obtained by treating sulfuric acid with a precipitate formed by adding calcium carbonate to tin. It is also called dioxysuccinic acid, because it is contained in tin precipitated when making wine. Represented by the formula $C_4H_6O_6$. There are several isomers of the right-turnable L-tartaric acid, the left-turnable D-tartaric acid, the racemic tartaric acid (also called the grape acid) which present equally, and m-tartaric acid which have no optical activity. When present naturally, L-tartaric acid is predominant, and it is widely distributed in plant system as free acid, calcium salt and potassium salt.

In one embodiment of the present invention, the term "pharmaceutical composition" refers to a composition that is administered for a specific purpose. For the purpose of the present invention, the pharmaceutical composition according to the present invention is a botulinum toxin composition comprising arginine, glutamic acid, or aspartic acid as a stabilizer, or comprising gluconolactone buffer, or tartaric acid buffer as a stabilization buffer, and may comprise a protein and a pharmaceutically acceptable carrier, excipient or diluent, which are involved in this administration. The term "pharmaceutically acceptable" carrier or excipient means approved by a regulatory agency of a government or listed in the Pharmacopeia or other generally recognized pharmacopeia for use in mammals, and more particularly in humans. For parenteral administration, the pharmaceutical composition of the present invention may be in the form of suspensions, solutions or emulsions in oily or aqueous carriers, and may be prepared in the form of solid or semi-solid. More preferably, it may be a liquid form. In addition, the pharmaceutical composition of the present invention may contain formulating agents such as suspending agents, stabilizers, solubilizing agents and/or dispersing agents, and may be sterilized. The pharmaceutical composition can be stable under the conditions of manufacture and storage, and can be preserved against the contaminating action of microorganisms such as bacteria or fungi. Alternatively, the botulinum toxin composition comprising arginine as a stabilizer according to the present invention may be in the form of sterile powder for reconstitution with suitable carriers before use. The pharmaceutical composition may be present in unit-dose form, microneedle patches, in ampoules, or other unit-dose containers or in multi-dose containers. Alternatively, the pharmaceutical composition can be stored in a freeze-dried (lyophilized) condition requiring only the addition of sterile liquid carrier, for example, water for injections, immediately prior to use. Extemporaneous injection solutions and suspensions can be prepared from sterile powders, granules or tablets.

In some non-limiting embodiments, the botulinum toxin composition containing arginine as a stabilizer according to the present invention may be formulated as liquid, or may be contained in the form of microspheres in liquid. In any non-limiting embodiments, the botulinum toxin composition containing arginine as a stabilizer may contain a botulinum toxin or a pharmaceutically acceptable compound and/or mixture thereof at a concentration of 0.001-100,000 U/kg. In any non-limiting embodiments, excipients suitable for the botulinum toxin composition containing arginine as a stabilizer include preservatives, suspending agents, stabilizers, dyes, buffers, antibacterial agents, antifungal agents, isotonic agents (for example, sugars or sodium chloride), and additional stabilizer. As used herein, the term "additional stabilizer" refers to a additionally contained stabilizer except for the present invention's stabilizer (arginine, glutamic acid, or aspartic acid) or stabilization buffer (gluconolactone buffer or tartaric acid buffer). That "additional stabilizer" is available without limitation as long as it is generally known in the art. Also the pharmaceutical composition according to the present invention may contain one or more pharmaceutically acceptable carriers. The carrier can be a solvent or dispersion medium. Non-limiting examples of pharmaceutically acceptable carriers include water, saline, ethanol, polyol (e.g., glycerol, propylene glycol and liquid polyethylene glycol), oils, and suitable mixtures thereof. Non-limiting examples of sterilization techniques that are applied to the pharmaceutical composition of the present invention include filtration through a bacterial-retaining filter, terminal sterilization, incorporation of sterilizing agents, irradiation, sterile gas irradiation, heating, vacuum drying, and freeze drying.

In one embodiment of the present invention, the term "administration" means introducing the composition of the present invention into a patient by any suitable method. The composition of the present invention may be administered via any general route, as long as it can reach a target tissue. The composition of the present invention can be administered orally, intraperitoneally, intravenously, intramuscularly, subcutaneously, intracutaneously, intranasally, intrapulmonarily, intrarectally, or intrathecally. However, the botulinum toxin composition according to the present invention is most preferably administered by intramuscular injection as a liquid formulation, but is not limited thereto.

A treatment method according to the present invention may comprise administering a pharmaceutically effective amount of the pharmaceutical composition. In the present invention, the effective amount can vary depending on various factors, including the kind of disease, the severity of the disease, the kinds and contents of active ingredient and other ingredients contained in the composition, the kind of formulation, the patient's age, weight, general health state, sex and diet, administration time, the route of administration, the secretion rate of the composition, the period of treatment, and drugs used concurrently.

In one embodiment of the present invention, there is provided a pharmaceutical formulation, containing: a neurotoxin, and a stabilizer. In the pharmaceutical composition, the neurotoxin may be any one or more selected from the group consisting of botulinum toxin, tetanus toxin, cholera toxin, and pertussis toxin. The botulinum toxin may be selected from the group consisting of botulinum toxin type A, B, C, D, E, F and G. The botulinum toxin is preferably botulinum toxin type A. In addition, the botulinum toxin may be either a form containing no complexing protein or a complex form containing a complexing protein. In the pharmaceutical formulation, the stabilizer is any one or more selected from arginine, glutamic acid, and aspartic acid, and the stabilizer is provided in the form of a stabilizing buffer, wherein the stabilizing buffer is any one or more selected from gluconolactone buffer, and tartaric acid buffer. In addition, the stabilizer may be contained at a concentration of 0.01-1,000 mM per 100 units of the botulinum toxin. The pharmaceutical formulation may have a pH of 5.5-7.0. In addition, the pharmaceutical formulation may further contain a local anesthetic. In the pharmaceutical formulation, the local anesthetic may be lidocaine, and may be contained in an amount of 0.1-1 wt % based on the total weight of the pharmaceutical formulation. In addition, the pharmaceutical formulation may further contain polysorbate. Additionally, the pharmaceutical formulation may be liquid.

In another embodiment of the present invention, there is provided a method for preparing a pharmaceutical formulation, comprising the steps of: (a) purifying a neurotoxin; and (b) adding a stabilizer to the neurotoxin. In the method, the neurotoxin may be preferably botulinum toxin type A. In the method, the stabilizer is any one or more selected from arginine, glutamic acid, and aspartic acid, and the stabilizer is provided in the form of a stabilizing buffer, wherein the stabilizing buffer is any one or more selected from gluconolactone buffer, and tartaric acid buffer. Additionally, the pharmaceutical formulation may be liquid.

Hereinafter, each step of the present invention will be described in detail.

Advantageous Effects

Botulinum toxin inhibits the exocytosis of acetylcholine at the cholinergic presynapse of a neuromuscular junction in animals having neurological function to thereby cause asthenia. Botulinum toxin has great therapeutic effects on various diseases due to its neurotoxic function, but is lethal even in a very small amount due to its strong toxicity. For this reason, when botulinum toxin is to be used in a living body, it is necessary to minutely control the concentration of botulinum toxin. However, currently available pharmaceutical compositions containing botulinum toxin have problems associated with protein denaturation. Due to such problems, the current pharmaceutical compositions are prepared and distributed in the form of freeze-dried formulations and diluted in liquid saline by the user immediately before use in clinical applications. For this reason, in the case of the current pharmaceutical compositions, there was a problem in that the risk of medical accidents caused by human errors such as dilution factor error or contamination of the dilution saline is high.

A pharmaceutical composition comprising botulinum toxin according to the present invention may contain arginine, glutamic acid, or aspartic acid as a stabilizer, or may contain gluconolactone buffer, or tartaric acid buffer as a stabilization buffer for botulinum toxin. And the composition of the present invention exhibited a remarkable effect on the stabilization of botulinum toxin even when it was distributed as a liquid formulation. Thus, it is expected that the composition of the present invention will greatly contribute to the safe and convenient medical use of botulinum toxin.

DESCRIPTION OF DRAWINGS

FIG. 1 shows the results of measuring the residual potency of botulinum toxin after incubating the botulinum toxin together with arginine or methionine for 28-56 days.

FIG. 2 shows the results of measuring the residual potency of botulinum toxin after incubating a botulinum toxin composition containing arginine or methionine at a pH of 6.0 to 7.0 for 56 days. pH 6.0 in FIG. 2a, pH 6.5 in FIG. 2b, pH 7.0 in FIG. 2c.

FIG. 3 shows the results of measuring the residual potency of botulinum toxin after incubating botulinum toxin compositions containing various antioxidants for 28 days.

FIG. 4 shows the results of measuring the residual potency of botulinum toxin after incubating botulinum toxin compositions containing various buffers for 28 days.

FIG. 5 shows each step of a DESCR assay for measuring the potency of botulinum toxin according to one example of the present invention.

FIG. 6 shows the results of comparing the effects of arginine and methionine on the stabilization of liquid botulinum formulations according to one example of the present invention. Specifically, FIG. 6a shows comparison results for formulations containing no local anesthetic, and FIG. 6b shows comparison results for formulations containing a local anesthetic (0.3% lidocaine).

FIG. 7 shows the results of evaluating the effect of the material of a liquid formulation container on the stabilization of BoNT/A efficacy. Specifically, FIG. 7a shows evaluation results for formulations containing no local anesthetic, and FIG. 7b shows evaluation results for formulations containing a local anesthetic (0.3% lidocaine).

FIG. 8 shows the results of comparing the stabilizing effect of arginine on formulations containing a tartaric acid or gluconolactone as a buffer by use of a glass container according to one example of the present invention. Specifically, FIG. 8a shows comparison results for formulations containing no local anesthetic, and FIG. 8b shows comparison results for formulations containing a local anesthetic (0.3% lidocaine).

FIG. 9 shows the results of evaluating the effect of arginine as a stabilizer on formulations containing glutamic acid in addition to a tartaric acid or gluconolactone buffer according to one example of the present invention. Specifically, FIG. 9a shows evaluation results for formulations containing no local anesthetic, and FIG. 9b shows evaluation results for formulations containing a local anesthetic (0.3% lidocaine).

FIG. 10 shows the results of evaluating the optimum concentration of glutamic acid that contributes to the stabilizing effect of arginine on formulations containing gluconolactone as a buffer according to one example of the present invention. Specifically, FIG. 10a shows evaluation results for formulations containing no local anesthetic, and FIG.

10b shows evaluation results for formulations containing a local anesthetic (0.3% lidocaine).

FIG. 11 shows the results of evaluating the effect of aspartic acid on the BoNT/A stabilizing efficacy of arginine according to one example of the present invention. Specifically, FIG. 11a shows evaluation results for formulations containing no local anesthetic, and FIG. 11b shows evaluation results for formulations containing a local anesthetic (0.3% lidocaine).

FIG. 12 shows the results of comparing the stability of a BoNT/A product prepared from a liquid formulation having a novel composition when arginine or methionine is added to the product, according to one example of the present invention.

BEST MODE

The results of the experiment performed in the present invention showed that the stabilizing effects of arginine and methionine on botulinum toxin were pH-dependent. Based on these results, the pH of liquid BoNT/A formulations was set to 6.0, and the concentration of arginine in the liquid BoNT/A formulations was changed to various concentrations. BoNT/A was added to the formulations to an initial potency of 80 units/ml, and then the formulations were incubated at 37° C. for 8 weeks, and the potency of the BoNT/A was measured by a DESCR assay. As a result, it was shown that the residual potency of the BoNT/A in the control group containing no stabilizer was 10% after 2 weeks, and the experimental group containing 50 mM methionine showed residual potencies of 67%, 47% and 27% after 2 weeks, 4 weeks and 8 weeks, respectively. This demonstrated that methionine has a significant stabilizing effect. Meanwhile, arginine showed a stabilizing effect greater than methionine at a concentration of 50 to 100 mM, and the residual potency of the BoNT/A in the formulation containing methionine was 31 to 65% even after 8 weeks.

MODE FOR INVENTION

Hereinafter, the present invention will be described in further detail with reference to examples. It will be obvious to those skilled in the art that these examples are for illustrative purposes only and are not intended to limit the scope of the present invention.

The sources of all reagents used in the examples of the present invention are listed in the following (*).

* Gluconolactone (Sigma G2164); L(+)-tartaric acid (Merck 100804); lidocaine hydrochloride monohydrate (Sigma L5647); octanoic acid (Sigma C2875); L-methionine (Merck K45023607 414); L-arginine (Merck K45895542 534); glycine (Bioshop GLN001-1); L-Glutamic acid (Merck 100291); aspartic acid (Merck K45895542 534); maleic acid (Merck S6858580 534); butylated hydroxyanisole (Sigma SLBM1210V); propyl gallate (Sigma P3130); sodium bisulfite (Sigma MKBR6468V); thioglycolic acid (Sigma T3758); L-cystein hydrochloride (K46446495 513); succinic acid (Merck K46618782 533); sodium phosphate monobasic (Sigma S5011); sodium phosphate dibasic (Sigma S7907); sodium chloride (Merck K47013904 548); polysorbate (Sigma P7949); and DL-dithiothreitol (Sigma D0632).

The abbreviations and the composition of the buffer used in the examples of the present invention are listed in the following (**).

** L-methionine (Met, or "M"), L-arginine (Arg, or "R"), L-Glutamic acid (Glu, or "E"), aspartic acid (Asp, or "D"), Buffer P (10 mM NaPO$_4$, pH 6.0, 45 mM NaCl, and 0.05% polysorbate), Buffer G (10 mM gluconolactone, pH 6.0, 45 mM NaCl, and 0.05% polysorbate), Buffer R (buffer G supplemented with 50 mM arginine).

Example 1: Development of Botulinum Toxin Stabilizer Using BoTest

Example 1-1: Preparation of Experiments

A botulinum toxin used in the present invention was one produced by Hugel Pharma Co., Ltd. (Korea) and adjusted to a concentration of 0.1 mg/ml and potency of 1,529 units/μl (based on the BoTest). In all experiments for identification of additives having a stabilizing effect, the botulinum toxin was used after it was diluted to 50 units/μl with a "protein dilution buffer" having a composition (50 mM NaPO$_4$, pH 7.0, 1 mM DTT, 0.05 wt % polysorbate, and 20 wt % glycerol).

For identification of additive candidates having a stabilizing effect, each experimental group (100 μl) was prepared by diluting 200 units of the botulinum toxin and a stabilizer additive candidate in a "stabilizing liquid composition (10 mM NaPO$_4$ (pH 5.5-7.0), 0.01 wt % polysorbate, 130 mM NaCl)". Then, each experimental group was incubated at a temperature of 37° C. for 1-11 weeks, and a portion (25%) thereof was used for measurement of the residual potency thereof. The potency of the botulinum toxin was measured using a BoTest® Botulinum Neurotoxin Detection Kit (BioSentinel, USA). For this, 5 mM HEPES-NaOH (pH 7.1), 0.1 wt % polysorbate, 10 uM ZnCl$_2$ (Sigma 229997), 0.2 uM BoTest A/E reporter, and 25 μl stabilizing experimental group were mixed with one another to prepare a final reaction solution (100 μl), and the reaction solution was incubated at 37° C. for 21 hours. The CFP/FRET ratio of the incubated reaction solution was measured using a Synergy Neo2 Multi-Mode Reader (BioTek, USA) system and applied to a standard curve, thereby determining the residual potency of the botulinum toxin. In addition, all reagents used in the study on stabilization of the botulinum toxin according to the present invention were dissolved in triple-distilled water and adjusted to a pH of 5.5-7.0 by the addition of hydrochloric acid and sodium hydroxide.

Example 1-2: Comparison of Stabilizing Effects of Arginine or Methionine at Varying pHs The effects of arginine and methionine as stabilizers on the stabilization of botulinum toxin at a pH ranging from 5.5 to 7.0 were comparatively examined.

For this, botulinum toxin was added to the stabilizing liquid composition described in Example 1, and 50 mM of arginine or methionine was further added to the liquid composition. The resulting composition was incubated at 37° C. for 28-56 days, and then the residual potency of the botulinum toxin was measured. The results of the measurement are shown in Table 1 below and FIG. 1.

TABLE 1

|  |  | 0 day | 28 days | 56 days |
| --- | --- | --- | --- | --- |
| pH 5.5 | 50 mM arginine | 100 | 34.2 | 27.5 |
|  | 50 mM methionine | 100 | 1.22 | 9.01 |
|  | Negative control | 100 | 0.97 | −0.34 |
| pH 6.0 | 50 mM arginine | 100 | 28.2 | 32.6 |
|  | 50 mM methionine | 100 | 7.5 | −0.66 |
|  | Negative control | 100 | 8.38 | −0.63 |

TABLE 1-continued

|  |  | 0 day | 28 days | 56 days |
|---|---|---|---|---|
| pH 6.5 | 50 mM arginine | 100 | 23.6 | 16.2 |
|  | 50 mM methionine | 100 | 13.6 | 8.78 |
|  | Negative control | 100 | −1.06 | −0.8 |
| pH 7.0 | 50 mM arginine | 100 | 19.6 | 1.72 |
|  | 50 mM methionine | 100 | 1.63 | −0.94 |
|  | Negative control | 100 | −0.83 | 0.11 |

As can be seen from the experimental results, in the negative control group containing no stabilizing candidate, the botulinum toxin was unstable at all the pHs, and thus the residual potency of the botulinum toxin was not substantially detected after 28 days. The experimental group containing methionine as a stabilizer a residual potency of about 10% at pH 5.5 to 7.0, whereas the experimental group containing arginine showed a residual potency of up to 30%. In addition, it was measured that the effect of arginine on the stabilization of the botulinum toxin was higher at a pH ranging from 5.5 to 6.0 than at a pH ranging from 6.5 to 7.0.

Example 1-3: Comparative Examination of Stabilizing Effects of Arginine or Methionine In order to verify the effect of arginine or methionine on the stabilization of botulinum toxin, a botulinum toxin composition containing arginine (50 mM) or methionine (50 mM) as a stabilizing additive was incubated for 56 days, and the residual potency of the botulinum toxin was measured in three independent experiments. The results of the measurement were statistically processed, thereby comparatively verifying the effects of arginine and methionine. As a control group, a sample containing no additive was used. To determine the significance between the three experimental groups, the one-way ANOVA method was used. When the significance probability (p-value) was 0.05 or less, it was determined that there was a significant difference between the three experimental group, and post-hoc analysis was performed by the LSD (Least Significant Difference) method. The results of the measurement are shown in Table 2 below and FIG. 2.

TABLE 2

|  |  | Stabilization at 37° C. | | | |
|---|---|---|---|---|---|
|  | pH | 0 day | 14 days | 28 days | 56 days |
| 50 mM arginine | 6.0 | 100 | 90.1 ± 5.5 | 71.6 ± 7.5** | 69.1 ± 14** |
|  | 6.5 | 100 | 71.9 ± 2.1* | 70.6 ± 9.6** | 38.4 ± 8.2** |
|  | 7.0 | 100 | 70.1 ± 9** | 55.8 ± 8.2*** | 16.9 ± 6.8* |
| 50 mM methionine | 6.0 | 100 | 57.6 ± 12 | 27.2 ± 8.3 | 22.6 ± 8.5 |
|  | 6.5 | 100 | 55 ± 4.4 | 36.7 ± 3.3 | 11.1 ± 3.8 |
|  | 7.0 | 100 | 40.2 ± 2.7 | 17.1 ± 4.3 | 0.35 ± 1.4 |
| Negative control | 6.0 | 100 | 47 ± 14 | 21.7 ± 5.6 | −1.22 ± 0.2 |
|  | 6.5 | 100 | 29.1 ± 7.5 | 17.3 ± 6.9 | −1.27 ± 0.3 |
|  | 7.0 | 100 | 5.16 ± 4.8 | 3.37 ± 2.7 | 1.37 ± 0.6 |

The results obtained in this Example indicate that arginine and methionine all show the high stabilizing effect at a pH of 6.0, and these experimental results are consistent with the above-described experimental results. However, under the same pH condition, arginine showed a higher stabilizing effect compared to methionine in all the experimental groups. For example, in the control group containing no stabilizer, the potency of the botulinum toxin was not measured under all conditions after 56 days of incubation, but in the experimental group containing methionine, a residual potency of 22.6% was measured at a pH of 6.0, and in the experimental group containing arginine, a potency of 69.1% was measured under the same condition.

The significance of the relative stabilizing effect of arginine and methionine was examined using the one-way ANOVA method, and as a result, it was shown that, at a pH of 6.0, the stabilizing effect values were significant in all the experimental groups except for the experimental group incubated for 14 days. For such results, post-hoc analysis was performed by the LSD (Least Significant Difference) method, and as a result, it was shown that the stabilizing effect of arginine was significantly better than that of methionine at a level of $p<0.05$ to $p<0.001$. For example, the comparison of values measured after 28 days of incubation at a pH of 7.0 indicated that the experimental group containing methionine showed a residual potency of 17.1% and the experimental group containing arginine showed a residual potency of 55.8%, and thus there was a significant difference of $p<0.001$ in the stabilizing effect between the two groups. In addition, the comparison of values measured after 56 days of incubation at a pH of 6.0 indicated that the experimental group containing methionine showed a residual potency of 22.6% and the experimental group containing arginine showed a residual potency of 69.1%, and thus there was a significant difference of $p<0.01$ in the stabilizing effect between the two groups.

And the present inventors examined the effect of the surfactant property of polysorbate on the stabilizing effect of botulinum toxin when methionine or arginine is added. For this, the botulinum toxin and 50 mM of arginine or methionine were added to a stabilizing liquid composition containing 0-0.05 wt % of polysorbate, and the resulting composition was incubated at 37° C. for 28-56 days, after which the residual potency of the botulinum toxin was measured. From the experimental results, in the case of the stabilizing composition containing methionine, at a pH ranging from 5.5 to 6.0, the stabilizing effect showed a tendency to increase in proportion to the concentration of polysorbate, and at a pH ranging from 6.5 to 7.0, the effect of polysorbate generally did not appear. In the case of the experimental group containing arginine, at a pH ranging from 5.5 to 6.5, the addition of polysorbate showed a tendency to contribute to the stabilizing effect, but the effect of polysorbate was not so significant. Such results suggest that the addition of polysorbate to a liquid botulinum toxin formulation containing arginine as a stabilizer is not essential.

Example 1-4: Identification of New Stabilizers for Liquid Formulation of Botulinum Toxin The results of Examples 1-2 to 1-3 indicate that arginine has a better effect on the stabilization of a liquid formulation of botulinum toxin compared to methionine. However, detection of new additives showing effects similar to that of arginine enables the development of various products. For this, the present inventors comparatively examined the botulinum toxin-stabilizing effects of various stabilization candidates shown in Table 3 below. The results of the examination are shown in FIG. 3, and FIG. 4.

TABLE 3

| Candidate for stabilization of botulinum toxin | Stabilizing effect |
|---|---|
| Arginine | +++ |
| Gluconolactone | ++ |

TABLE 3-continued

| Candidate for stabilization of botulinum toxin | Stabilizing effect |
|---|---|
| Glycine | – |
| Tartaric acid | ++ |
| Sodium bisulfite | – |
| Cysteine | – |
| Propyl gallate | – |
| Sodium hydrosulfite | + |
| Thioglycolate | – |

FIG. 3 shows the results of measuring the residual potency of botulinum toxin after 28 days of culture of botulinum toxin compositions containing the antioxidants shown in Table 3 above. The results of the measurement indicated that all the antioxidant additives used in the examination showed stabilizing effects lower than that of the control methionine. However, in the case of the buffers, gluconolactone showed a significant stabilizing effect at a pH of 6.5, and tartaric acid showed a stabilizing effect at a pH ranging from 5.5 to 6.5 (FIG. 4). Such results suggest the possibility of development of new additives having remarkable effects.

Example 2. Development of Botulinum Toxin Stabilizer Using DESCR

Example 2-1. Preparation of Experiments

In Example 1, the liquid formulation sample containing the botulinum toxin having a relatively high potency (200 units/0.1 ml) was prepared in the polypropylene tube, and the residual potency of the botulinum toxin was measured using the BoTest assay. However, this botulinum toxin concentration significantly differs from the concentration of botulinum toxins which are commercially available for clinical use. Hence, in the present invention, studies on formulations for stabilization of botulinum toxin were performed using formulations having compositions similar to those of currently commercially available botulinum products, that is, formulations in which the initial potency of botulinum toxin is 40 to 80 units/ml. Since the BoTest assay requires a potency of at least 50 units, it cannot measure the residual potency of botulinum toxin in the liquid formulations prepared under the above-described conditions. Therefore, the present inventors have developed a DESCR (Direct ELISA coupled with in vitro SNAP25 cleavage reaction) method capable of quantitatively measuring the potency of BoNT/A present in trace amounts. The DESCR method will be described in detail in Example 2-2 below.

Briefly, although 200 units of BoNT/A was added to 100 μl of each liquid formulation sample and the residual potency thereof in all the formulation samples was measured by the BoTest assay in Example 1, 40 to 80 units/ml of BoNT/A was added to 0.1 to 1 ml of each liquid formulation sample and the residual potency thereof in all the formulation samples was measured by the DESCR method (newly developed by the present inventors) in Example 2.

For identification of additive candidates having a stabilizing effect, a sample of each experimental group, which contained 10 mM $NaPO_4$ (pH 6.0), 10 mM tartaric acid (pH 6.0) or 10 mM gluconolactone (pH 6.0) as a buffer, was used as a negative control, and all the formulation samples commonly contained 0.05% polysorbate, 45 to 130 mM NaCl, botulinum toxin and a stabilizer additive candidate. These formulation samples were incubated at 37° C. for 2 to 8 weeks, and 10 μl (0.4 units) of each formulation sample was used for the measurement of the residual potency of the botulinum toxin. Experimental methods whose detailed description was omitted were as described in Example 1 above.

Example 2-2. Development of DESCR Measurement Method

DESCR (Direct ELISA coupled with in vitro SNAP25 cleavage reaction) consists of the following two steps:

(1) performing an in vitro enzymatic reaction between BoNT/A and a highly pure recombinant protein (GST-SNAP25) as a substrate (in vitro SNAP25 cleavage reaction); and (2) quantitatively measuring the degree of the enzymatic reaction by enzyme-linked immunosorbent assay (ELISA).

The degree of the reaction is detected by a color reaction. Specifically, it can be detected by a color reaction using a primary antibody, which reacts specifically with a form (SNAP25197) cleaved by BoNT/A, and a HRP (horseradish peroxidase)-conjugated secondary antibody. Each of the steps is performed as follows.

(1) In Vitro SNAP25 Cleavage Reaction

The botulinum toxin used in the experiment was diluted to various concentrations (0, 0.2, 0.4, 0.6, 0.8, 1.2 and 1.6 units) and subjected to an enzymatic reaction in 20 μl of a buffer solution (20 mM HEPES-NaOH (pH 7.1), 0.1% Tween 20, 10 μM $ZnCl_2$, and 1 μg GST-SNAP25) at 37° C. for 21 hours.

(2) ELISA

80 μl of RSB (Reaction Stop Buffer; 125 mM carbonate (pH 9.6, Sigma S6014), and 6.25 mM EDTA) was added to the reaction solution in order to stop the BoNT/A reaction, and the reaction solution was transferred onto Maxisorp Immuno-plate (NUNC, Cat No. 170-6531), followed by coating at 37° C. for 2 hours. Each well was washed three times with WB (Washing Buffer; 1×PBS containing 0.05% Tween-20, and 0.2 M NaCl), and then blocked with BS (Blocking Solution; 5% skim milk in 1×PBS) at 37° C. for 15 minutes. Next, each well was washed once with WB, and 100 μl of $SNAP25_{197}$-specific antibody (1:250 dilution, R&D) diluted in BS was dispensed into each well and allowed to react at 37° C. for 1 hour. After washing three times with WB, 100 μl of HRP-conjugated secondary antibody (1:1000 dilution, AbFrontier, LF-SA8001) diluted in BS was dispensed into each well and allowed to react at 37° C. for 1 hour. After washing three times with WB, 100 μl of TMB substrate (Thermo-fisher, Cat No. 34028) was dispensed into each well to induce a color reaction. The reaction was stopped by adding the same amount of 2M sulfuric acid (Sigma, Cat No. 258105), and the absorbance at 450 nm was measured using an absorption analyzer (Multi-Mode Reader Synergy Neo2, BioTek) system, and the AU value was calculated. These steps are schematically shown in FIG. 5.

Example 2-3. Comparison of the Effects of Arginine and Methionine on Stabilization of Liquid Botulinum Formulation The results of Example 1 showed that the stabilizing effects of arginine and methionine on botulinum toxin were pH-dependent. Specifically, in an experimental group containing methionine as a stabilizer, the botulinum toxin showed a residual potency of up to about 10% in the pH range of 5.5 to 7.0, but in an experimental group containing arginine, a residual potency of up to about 30% was measured. Furthermore, it was shown that the effect of arginine on the stabilization of BoNT/A was higher at a pH of 5.5 to 6.0 than at a pH of 6.5 to 7.0. In a negative control group containing stabilizer additive candidate, BoNT/A tended to be unstable under all the pH conditions, and thus the residual potency of BoNT/A was not detected after 28 days.

Based on these results, the pH of liquid BoNT/A formulations was set to 6.0, and the concentration of arginine in the liquid BoNT/A formulations was changed to various concentrations. BoNT/A was added to the formulations to an initial potency of 80 units/ml, and then the formulations were incubated at 37° C. for 8 weeks, and the potency of the BoNT/A was measured by a DESCR assay. The results of the measurement are shown in FIG. 6.

As a result, it was shown that the residual potency of the BoNT/A in the control group containing no stabilizer was 10% after 2 weeks, and the experimental group containing 50 mM methionine showed residual potencies of 67%, 47% and 27% after 2 weeks, 4 weeks and 8 weeks, respectively. This demonstrated that the methionine has a significant stabilizing effect. Meanwhile, arginine showed stabilizing efficacy higher than methionine at a concentration of 50 to 100 mM, and the residual potency of the BoNT/A in the formulation containing methionine was measured to be 31 to 65% even after 8 weeks. The difference in the relative stabilizing effects of methionine and arginine was also observed in formulations containing 0.3% lidocaine. In other words, after 8 weeks, an experimental group containing methionine showed a residual potency of 27%, and an experimental group containing arginine showed a residual potency of 44 to 62%.

The above results show that: (1) the stabilizing effect of arginine is verified regardless of various measurement methods, including the BoTest assay and the DESCR assay; (2) arginine exhibits a stabilizing effect even under the conditions of formulations containing a botulinum toxin having a potency similar to those of products which are actually prepared/distributed for clinical use; and (3) the stabilizing effect of arginine is maintained even in formulations containing lidocaine.

Example 2-4. Evaluation of the Effect of Liquid Formulation Container Material on Stabilization of BoNT/A Efficacy Example 2-3 above shows the results obtained by preparing the botulinum toxin-containing formulations in polypropylene tubes. However, since botulinum toxin liquid formulations that are actually distributed for clinical use are prepared in glass containers, the stabilizing effects of methionine and arginine on the residual potency of botulinum toxin were evaluated again using glass containers. Specifically, BoNT/A was prepared into liquid formulations having an initial potency of 40 units/ml and containing 20 mM methionine or 100 mM arginine, and the residual potency of the BoNT/A in the formulations was measured by the DESCR assay while the formulations were incubated at 37° C. for 8 weeks. The results of the measurement are shown in FIG. 7.

As a result, the residual potency of the BoNT/A in the formulation containing methionine was measured to be 41%, 15% and 8% after 2 weeks, 4 weeks and 8 weeks, respectively. Meanwhile, the residual potency of the BoNT/A in the formulation containing arginine was measured to be 84%, 64% and 43% after the same periods, and showed a great difference from the residual potency of the BoNT/A in the formulation containing methionine.

Even when the liquid formulations contained lidocaine, methionine and arginine all showed a stabilizing effect. Specifically, the residual potency of the BoNT/A in the formulation containing methionine was measured to be 47%, 21% and 16% after 2 weeks, 4 weeks and 8 weeks, respectively, and the residual potency of the BoNT/A in the formulation containing arginine was measured to be 79%, 71% and 55%, indicating that the stabilizing effect of arginine significantly differs from that of methionine. The above results show that: (1) the potency of BoNT/A in a formulation sample prepared in a polypropylene tube is more stably maintained than the potency of BoNT/A in a formulation sample prepared in a glass container, even if the formulations have the same composition; and (2) the stabilizing effect of arginine on a BoNT/A liquid formulation prepared in a glass container is better than that of methionine.

Example 2-5. Evaluation of the Effect of Buffer and Glutamic Acid on the Stabilizing Effect of Arginine Example 1-4 above indicated that tartaric acid and gluconolactone as buffers had a stabilizing effect and all exhibited the optimum effect at around pH 6.0. Accordingly, the stabilizing effect of arginine on BoNT/A formulations containing tartaric acid or gluconolactone as a buffer was examined using a glass container. A buffer used as a negative control was sodium phosphate ($NaPO_4$, pH 6.0) which is most generally used. The results of the comparison are shown in FIG. 8.

As a result, it was shown that the stabilizing effect of arginine showed similar patterns in all the liquid formulations, and the residual potency of BoNT/A in the formulations containing arginine was measured to be 57 to 70% even after 8 weeks. The stabilizing effect of arginine on the formulation containing gluconolactone among all the buffers used in the experiment was significantly high, and the residual potency of BoNT/A in this formulation was measured to be about 10% higher than those in other formulation samples. This tendency also appeared in formulations containing lidocaine.

In addition, the effect of arginine as a stabilizer in formulations containing glutamic acid in addition to a tartaric acid or gluconolactone buffer was evaluated. The results of the evaluation are shown in FIG. 9. In Example 2-3 above, it was shown that when 50 mM glutamic acid was added to the BoNT/A liquid formulation containing sodium phosphate buffer and 50 mM arginine, the residual potency of BoNT/A in the formulation was 65% after 8 weeks. When glutamic acid was not added to the formulation, the residual potency of BoNT/A in the formulation was 32%. A similar result was also obtained for a formulation containing lidocaine, and specifically, the residual potency of BoNT/A in this formulation was measured to be 71% after 8 weeks. In this case, when the formulation contained no glutamic acid, a residual potency of 45% was measured (see FIG. 6).

Based on the experimental results, in order to select the optimum buffer for stabilization of BoNT/A liquid formulations containing both arginine and glutamic acid, the efficacy of BoNT/A in formulations containing sodium phosphate, tartaric acid or gluconolactone was compared using glass containers. As a result, it was shown that the residual potency of DESCR, measured by the DESCR assay after 2 weeks, 4 weeks and 8 weeks, was significantly high in the formulation containing gluconolactone as a buffer. Specifically, when the formulation contained no lidocaine, the residual potencies after 2 weeks, 4 weeks and 8 weeks reached 96%, 87% and 71%, respectively, and when the formulation contained lidocaine, the residual potencies were measured to be 96%, 86% and 68%.

Finally, in order to evaluate the optimal concentration of glutamic acid that contributes to the stabilizing effect of arginine, 50 mM arginine and 10 to 50 mM glutamic acid were added to formulations containing gluconolactone as a buffer, and the efficacy of BoNT/A in the formulations was measured in polypropylene tubes. The results of the measurement are shown in FIG. 10. As a result, a significant level of BoNT/A efficacy was also detected in the formulations containing only glutamic acid without arginine, and the efficacy was more distinct in the formulations containing lidocaine. Specifically, the residual potency measured after 8 weeks of incubation at 37° C. was 15% in the negative control and 41% in the formulation containing glutamic acid alone. However, when glutamic acid was used alone, the effect thereof on the stabilization of BoNT/A was lower than that of arginine. Specifically, the formulation containing arginine alone showed a residual potency of 61% after 8 weeks of incubation at 37° C. The efficacy of BoNT/A in a formulation containing 10 to 50 mM glutamic acid together with 50 mM arginine was measured, and as a result, it was shown that the residual potencies measured after 2 to 8 weeks were very similar to those in the formulations containing arginine alone in almost all the experimental groups. This tendency also appeared in the formulations containing lidocaine. Specifically, the residual potency measured after 8 weeks of incubation was 61% in the formulation containing arginine alone, and was about 57 to 65% in the formulation containing both arginine and glutamic acid without showing a significant relationship with the concentration.

The above results suggest that the following important fact. Glutamic acid has the effect of stabilizing BoNT/A in liquid formulations, but the effect of glutamic acid alone is insignificant compared to the effect of arginine alone. A formulation containing both glutamic acid and arginine shows no synergistic effect even after a relatively long storage period of 8 weeks, and the residual potency of BoNT/A in this formulation is maintained at a constant level (60 to 80%).

Example 2-6. Evaluation of the Effect of Aspartic Acid on the Stabilizing Effect of Arginine as Stabilizer The effect of aspartic acid, which is an acidic amino acid such as glutamic acid, on the BoNT/A stabilizing effect of arginine, was examined, and the results are shown in FIG. 11. BoNT/A in formulations containing aspartic acid alone shows relatively high residual potency after 2 to 8 weeks of incubation, and this stabilizing effect of aspartic acid remarkably appears in formulations containing lodocaine. In the negative control group, the residual efficacy was measured to be 73%, 30% and 15% after 2 weeks, 4 weeks and 8 weeks, respectively, but in the experimental group containing aspartic acid, the residual potency was measured to be 88%, 73% and 52%. The residual potency of BoNT/A after 8 weeks in a formulation containing 10 to 50 mM aspartic acid together with 50 mM arginine was measured, and as a result, it was shown that the residual potency was 61% in the formulation containing arginine alone, and was about 58 to 73% in the formulation containing aspartic acid in addition to arginine without showing a significant relationship with the concentration. Unlike the residual potencies measured after 8 weeks, the residual potencies of BoNT/A measured after 2 to 4 weeks showed a statistically significant difference. Specifically, in the formulation containing arginine alone, the residual potency was measured to be 82% and 76% after 2 weeks and 4 weeks, respectively, but when aspartic acid was added to the formulation, the residual potency was measured to be 92 to 100% and 85 to 94%. In addition, in the formulations containing glutamic acid, a similar stabilizing effect appeared during the same period, but the degree of the effect was relatively low and the residual potency was measured to be 83 to 98% and 76 to 88%. The measurement results for the formulations containing aspartic acid are shown in Table 4 below, and the measurement results for the formulations containing glutamic acid are shown in Table 5 below.

TABLE 4

| | | | Stabilize at 37° C. | | |
| --- | --- | --- | --- | --- | --- |
| | | 0 weeks | 2 weeks | 4 weeks | 8 weeks |
| Buffer G | Without aspartic acid | 100 | 62.84 ± 10.78 (73.07 ± 7.70) | 29.66 ± 2.01 (48.66 ± 4.67) | 15.1 ± 2.37 (36.59 ± 0.22) |
| | +50 mM aspartic acid | 100 | 87.91 ± 4.25 (85.2 ± 4.16) | 72.66 ± 5.69 (75.08 ± 3.24) | 51.92 ± 5.47 (51.72 ± 6.04) |
| Buffer R | Without aspartic acid | 100 | 82.01 ± 6.89 (91.40 ± 6.30) | 75.96 ± 4.65 (80.36 ± 6.53) | 61.19 ± 4.20 (61.54 ± 3.88) |
| | +10 mM aspartic acid | 100 | 92.19 ± 3.98 (86.83 ± 3.10) | 85.28 ± 5.79 (85.49 ± 2.33) | 73.05 ± 79.67 (79.01 ± 6.61) |
| | +25 mM aspartic acid | 100 | 93.37 ± 4.53 (94.76 ± 3.94) | 86.92 ± 7.08 (84.87 ± 4.48) | 58.05 ± 3.37 (65.49 ± 11.48) |
| | +50 mM aspartic acid | 100 | 100 ± 0.24 (94.79 ± 4.49) | 94.90 ± 3.72 (89.70 ± 4.21) | 61.07 ± 1.63 (73.85 ± 4.43) |

TABLE 5

| | | | Stabilize at 37° C. | | |
| --- | --- | --- | --- | --- | --- |
| | | 0 weeks | 2 weeks | 4 weeks | 8 weeks |
| Buffer G | Without glutamic acid | 100 | 62.84 ± 10.78 (73.07 ± 7.70) | 29.66 ± 2.01 (48.66 ± 4.67) | 15.9 ± 2.37 (36.59 ± 10.22) |
| | +50 mM glutamic acid | 100 | 87.41 ± 5.42 (90.29 ± 4.95) | 78.30 ± 6.22 (71.09 ± 3.35) | 40.87 ± 6.04 (37.42 ± 4.78) |

TABLE 5-continued

|  |  | Stabilize at 37° C. | | | |
|---|---|---|---|---|---|
|  |  | 0 weeks | 2 weeks | 4 weeks | 8 weeks |
| Buffer R | Without glutamic acid | 100 | 82.01 ± 6.89 (91.46 ± 6.30) | 75.96 ± 4.65 (80.36 ± 6.53) | 61.19 ± 4.20 (61.54 ± 3.88) |
|  | +10 mM glutamic acid | 100 | 93.34 ± 4.55 (100 ± 2.63) | 88.21 ± 5.69 (92.39 ± 7.38) | 65.76 ± 4.53 (72.11 ± 3.92) |
|  | +25 mM glutamic acid | 100 | 87.69 ± 3.21 (92.53 ± 12.79) | 76.38 ± 3.73 (87.68 ± 6.37) | 64.85 ± 5.93 (67.83 ± 15.29) |
|  | +50 mM glutamic acid | 100 | 83.68 ± 5.85 (89.18 ± 5.39) | 81.34 ± 6.50 (86.83 ± 6.60) | 55.98 ± 3.93 (50.36 ± 3.40) |

Example 2-7. Confirmation of Stability of BoNT/A Product Prepared from Novel Liquid Formulation A novel liquid composition for BoNT/A, established based on the results of systematically and comparatively analyzing a variety of liquid injectable additives whose safety was confirmed by the present inventors, comprises 10 mM gluconolactone (pH 6.0), 45 to 130 mM sodium chloride, 50 mM arginine, 50 mM aspartic acid, and 0.05% polysorbate. In order to verify the safety of a liquid formulation by mouse $LD_{50}$ assay, a BoNT/A formulation having the above-described composition was prepared using a glass container so as to have an initial potential of 40 units/ml. A liquid formulation product containing methionine instead of arginine was used as a control, and the stabilities of the products were comparatively examined. The results of the examination are shown in FIG. 12. As a result, it was shown that the stability of the BoNT/A product prepared from the novel liquid composition was very similar to the result obtained in the in vitro study. Specifically, the residual potencies measured for this BoNT/A product after 2 weeks, 4 weeks and 8 weeks were 96%, 84% and 66%, respectively, and the residual potencies for the control after 2 weeks, 4 weeks and 8 weeks were 41%, 15% and 8%, respectively.

INDUSTRIAL APPLICABILITY

Botulinum toxin inhibits the exocytosis of acetylcholine at the cholinergic presynapse of a neuromuscular junction in animals having neurological function to thereby cause asthenia. Thus, efforts have recently been made to use the neurotoxicity of botulinum toxin for cosmetic or therapeutic purposes. However, botulinum toxin, a protein agent, has a problem in that it is not easy to formulate into pharmaceutical compositions and is also not easy to store, distribute and manage. This is attributable to the instability of the protein, and the problem is serious in the case of protein agents such as botulinum toxin, which are formulated into pharmaceutical compositions at a very low concentration.

A liquid formulation containing botulinum toxin and stabilizing agent according to the present invention can be can easily stored and distributed. It was proved a significant effect on the stabilization of botulinum toxin under suitable conditions according to the temperature and pH of the human body. Thus, it is expected that the pharmaceutical composition of the present invention will greatly contribute to the safe and convenient medical use of botulinum toxin.

The invention claimed is:

1. A pharmaceutical formulation, containing: a neurotoxin, a stabilizer and a local anesthetic.

2. The pharmaceutical formulation of claim 1, wherein the neurotoxin is any one or more selected from the group consisting of botulinum toxin, tetanus toxin, cholera toxin, and pertussis toxin.

3. The pharmaceutical formulation of claim 2, wherein the botulinum toxin is botulinum toxin type A.

4. The pharmaceutical formulation of claim 2, wherein the botulinum toxin is either a form containing no complexing protein or a complex form containing a complexing protein.

5. The pharmaceutical formulation of claim 1, wherein the stabilizer is any one or more selected from arginine, glutamic acid, aspartic acid, gluconolactone, and tartaric acid.

6. The pharmaceutical formulation of claim 1, wherein the local anesthetic is lidocaine.

7. The pharmaceutical formulation of claim 1, further containing polysorbate.

8. The pharmaceutical formulation of claim 1, which is liquid.

9. A method for preparing a pharmaceutical formulation, comprising the steps of:
 (a) purifying a neurotoxin; and
 (b) adding a stabilizer and a local anesthetic to the neurotoxin.

10. The method of claim 9, wherein the neurotoxin is any one or more selected from the croup consisting of botulinum toxin, tetanus toxin, cholera toxin, and pertussis toxin.

11. The method of claim 9, wherein the stabilizer is any one or more selected from arginine, glutamic acid, and aspartic acid, gluconolactone, and tartaric acid.

12. The method of claim 9, further adding polysorbate to the neurotoxin, stabilizer, and a local anesthetic.

13. The method of claim 9, further comprising subsequent to steps (a) and (b), adding a liquid as step (c).

* * * * *